(12) United States Patent
Wakana et al.

(10) Patent No.: US 10,436,807 B2
(45) Date of Patent: Oct. 8, 2019

(54) AUTHENTICATION SYSTEM AND AUTHENTICATION METHOD FOR DETECTING BREATH ALCOHOL

(71) Applicant: Hitachi, Ltd., Tokyo (JP)

(72) Inventors: Hironori Wakana, Tokyo (JP); Masuyoshi Yamada, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 78 days.

(21) Appl. No.: 15/689,129

(22) Filed: Aug. 29, 2017

(65) Prior Publication Data

US 2018/0074081 A1 Mar. 15, 2018

(30) Foreign Application Priority Data

Sep. 12, 2016 (JP) ................. 2016-177868

(51) Int. Cl.
| | | |
|---|---|---|
| *G06K 9/00* | (2006.01) | |
| *G01N 33/98* | (2006.01) | |
| *A61B 5/1171* | (2016.01) | |
| *H04N 5/232* | (2006.01) | |
| *H04N 5/225* | (2006.01) | |
| *A61B 5/08* | (2006.01) | |
| *A61B 5/00* | (2006.01) | |

(52) U.S. Cl.
CPC ............ *G01N 33/98* (2013.01); *A61B 5/082* (2013.01); *A61B 5/1176* (2013.01); *A61B 5/4845* (2013.01); *G06K 9/00255* (2013.01); *G06K 9/00288* (2013.01); *G06K 9/00899* (2013.01); *H04N 5/2252* (2013.01); *H04N 5/232* (2013.01)

(58) Field of Classification Search
None
See application file for complete search history.

(56) References Cited

U.S. PATENT DOCUMENTS

| | | | | |
|---|---|---|---|---|
| 10,004,431 | B2* | 6/2018 | Shuster | A61B 5/1123 |
| 2008/0123907 | A1* | 5/2008 | Eura | G06K 9/00288 |
| | | | | 382/118 |
| 2009/0060287 | A1* | 3/2009 | Hyde | A61B 5/0002 |
| | | | | 382/118 |
| 2009/0090577 | A1* | 4/2009 | Takahashi | A61B 5/117 |
| | | | | 180/272 |
| 2009/0293589 | A1* | 12/2009 | Freund | A61B 5/18 |
| | | | | 73/23.3 |

(Continued)

FOREIGN PATENT DOCUMENTS

JP 2009255864 11/2009

OTHER PUBLICATIONS

Extended European Search Report received in corresponding European Application No. 17190038.4 dated Feb. 5, 2018.

*Primary Examiner* — Fernando Alcon
(74) *Attorney, Agent, or Firm* — Mattingly & Malur, PC

(57) ABSTRACT

It is an object to prevent impersonation in breath measurement by using a portable device. After breath is introduced into a breath introduction inlet 11 of a breath introduction device 1, a first image group is acquired by continuously capturing images over a predetermined period, and after drinking determination based on the introduced breath from the breath introduction inlet 11, the portable device is provided with an imaging device 11 that acquires a second image by capturing an image again and outputs whether or not each image in the first image group and the second image are the images of the same person.

13 Claims, 22 Drawing Sheets

(56) References Cited

U.S. PATENT DOCUMENTS

| | | | |
|---|---|---|---|
| 2011/0050407 A1* | 3/2011 | Schoenfeld | A61B 10/0051 340/426.11 |
| 2012/0268268 A1* | 10/2012 | Bargero | H04M 1/72527 340/539.11 |
| 2013/0035602 A1* | 2/2013 | Gemer | A61B 5/0404 600/484 |
| 2014/0311215 A1* | 10/2014 | Keays | B60K 28/063 73/23.3 |
| 2014/0320285 A1* | 10/2014 | Keays | G01N 33/4972 340/539.12 |
| 2015/0051502 A1* | 2/2015 | Ross | H04N 5/772 600/532 |
| 2015/0165903 A1* | 6/2015 | Williams | B60K 28/063 701/36 |
| 2015/0212063 A1* | 7/2015 | Wojcik | G01N 33/4972 340/576 |
| 2015/0233897 A1* | 8/2015 | Hok | G01N 21/3504 73/23.3 |
| 2016/0086021 A1* | 3/2016 | Grohman | G06K 9/00288 701/36 |
| 2017/0057353 A1* | 3/2017 | Griffin | B60K 28/063 |
| 2018/0101721 A1* | 4/2018 | Nienhouse | G06N 7/005 |
| 2018/0164285 A1* | 6/2018 | Nothacker | G01N 33/4972 |

* cited by examiner

[Fig. 1]
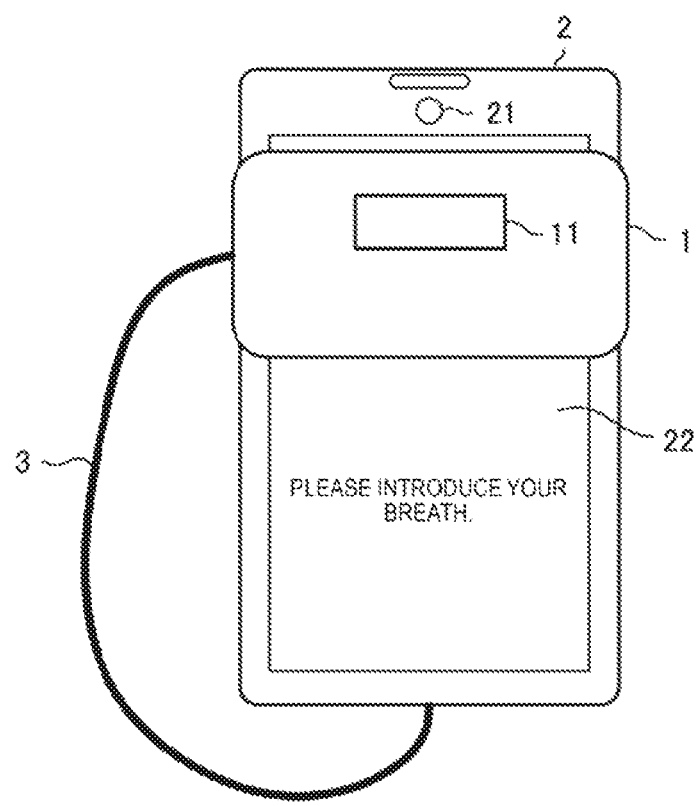

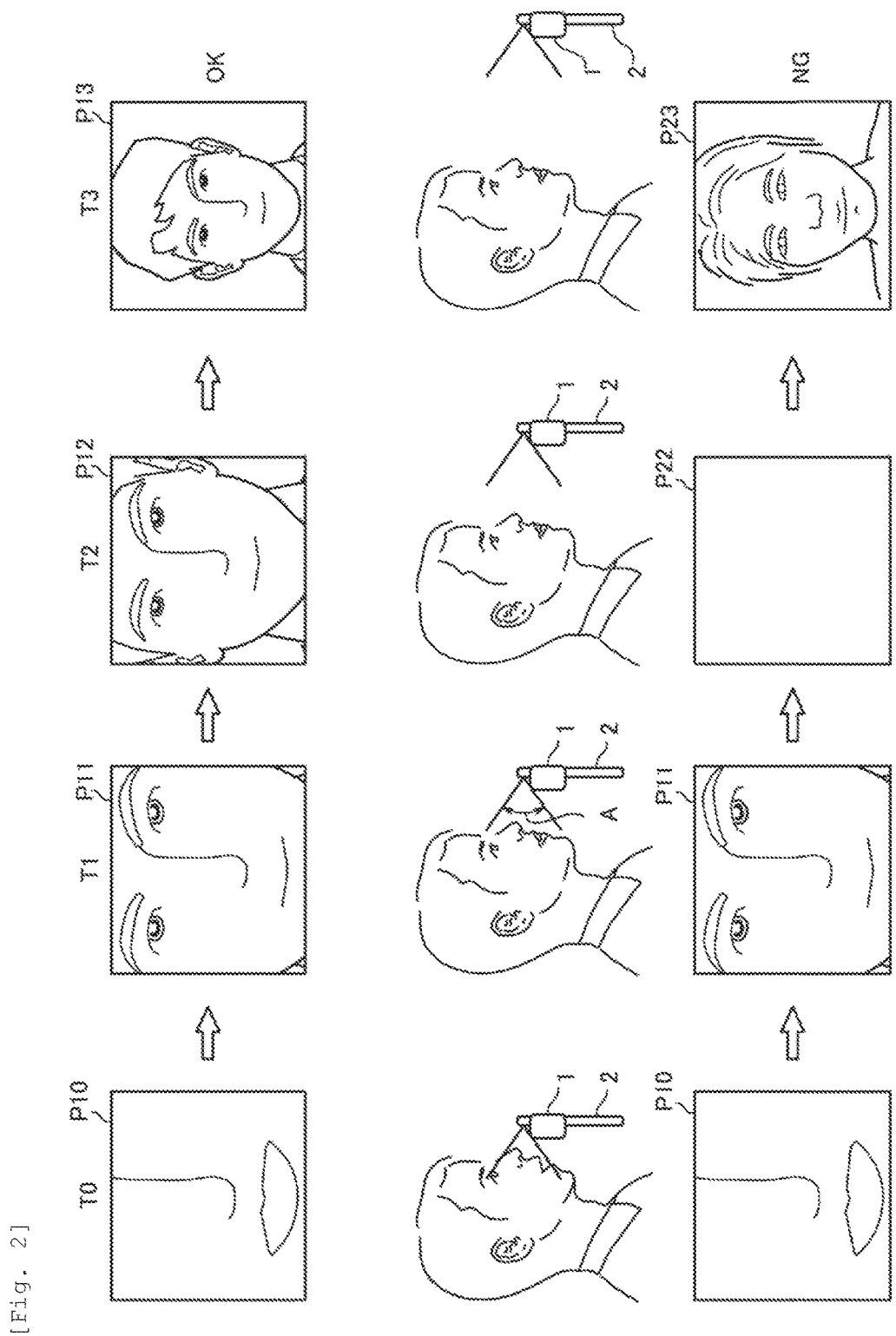
[Fig. 2]

[Fig. 3]
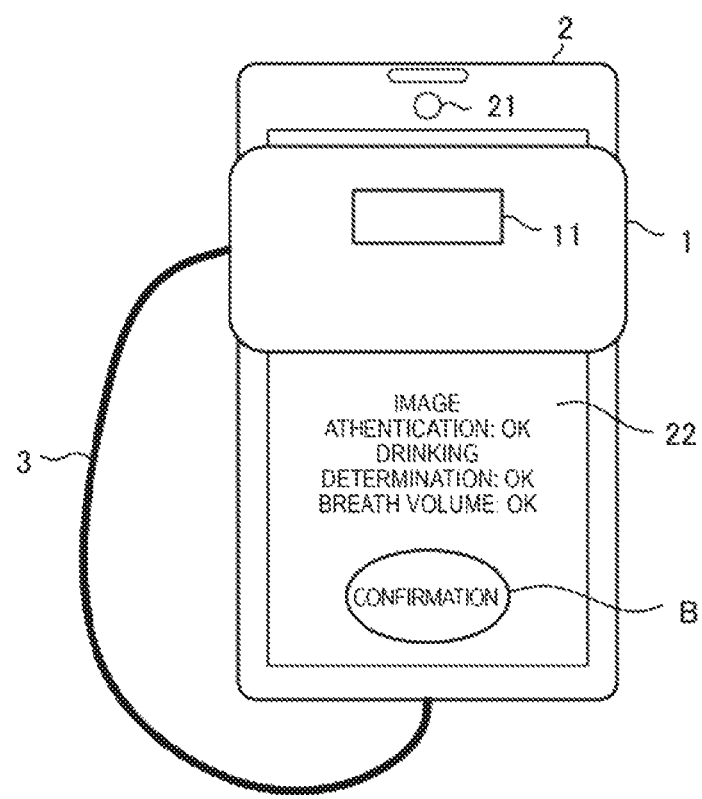

[Fig. 4]
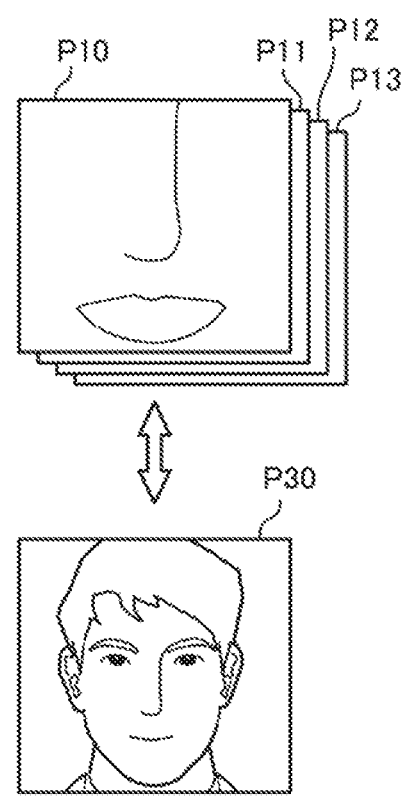

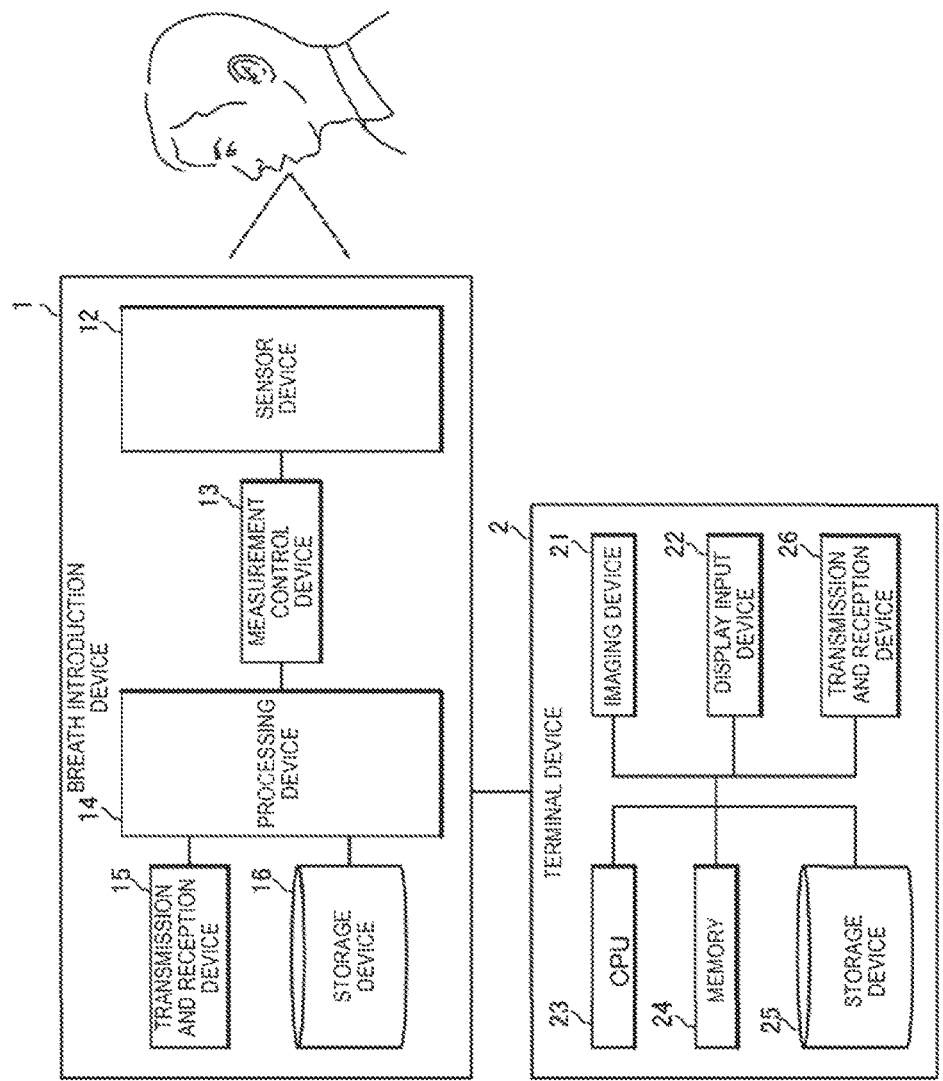
[Fig. 6]

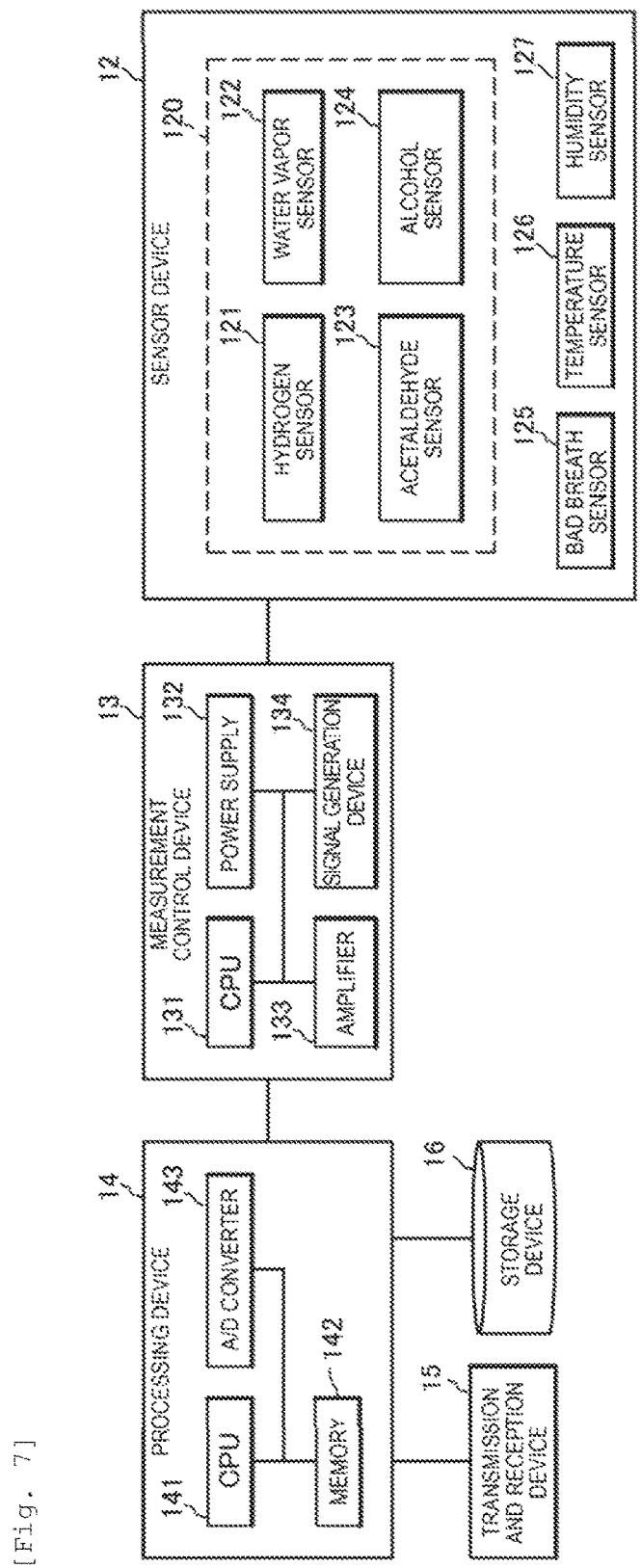
[Fig. 7]

[Fig. 8]
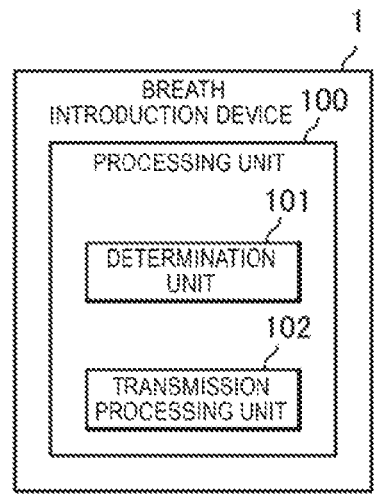
[Fig. 9]
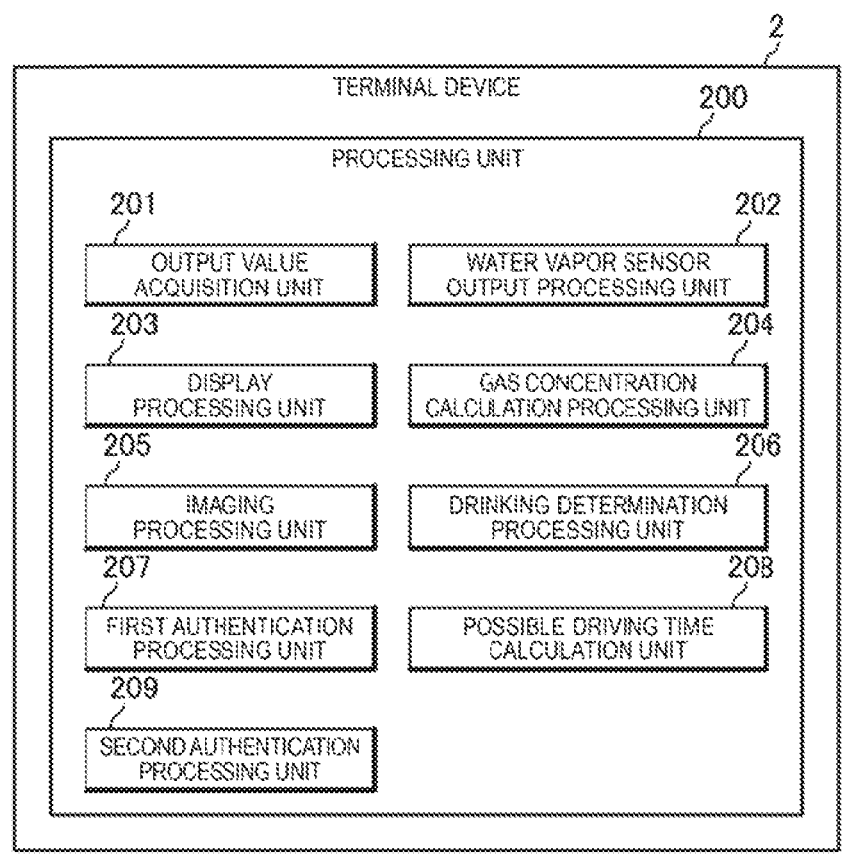

[Fig. 10]
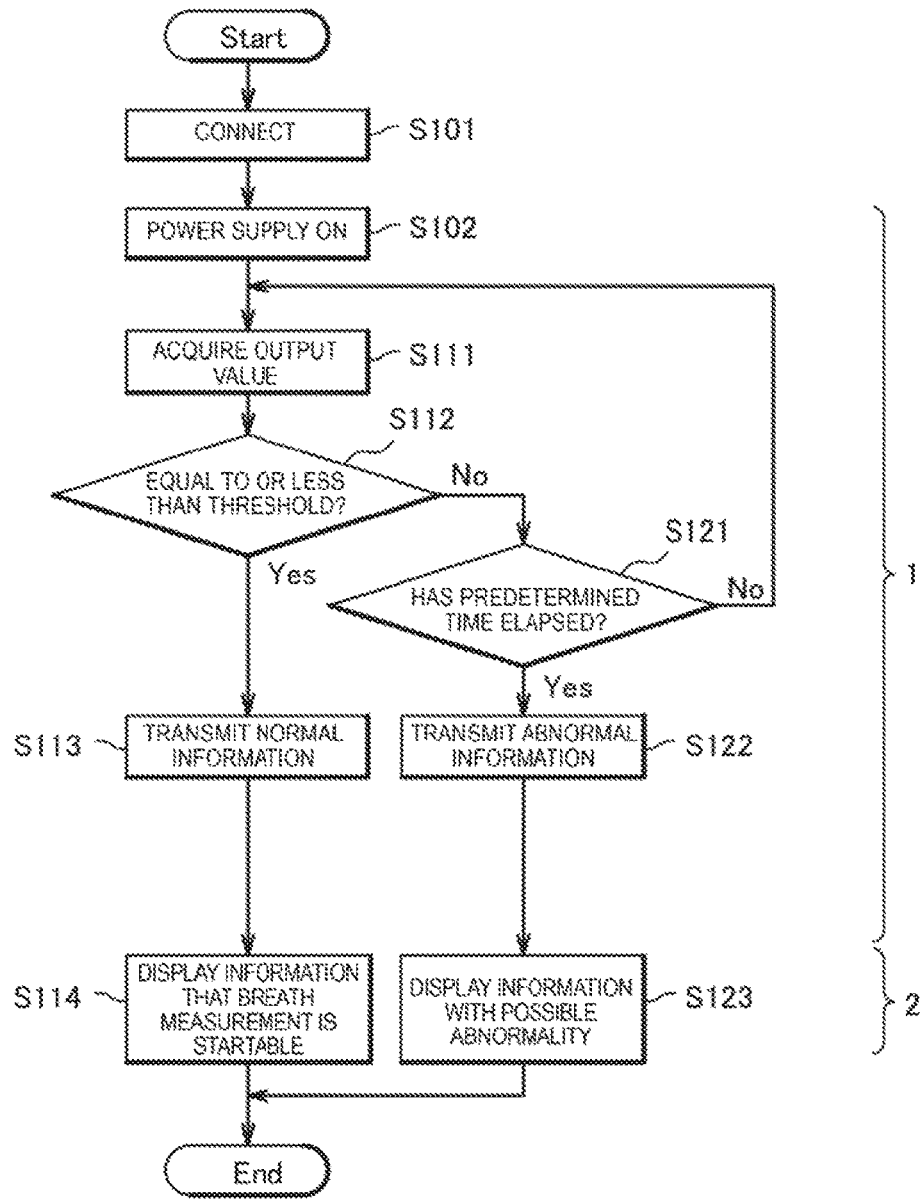

[Fig. 11]
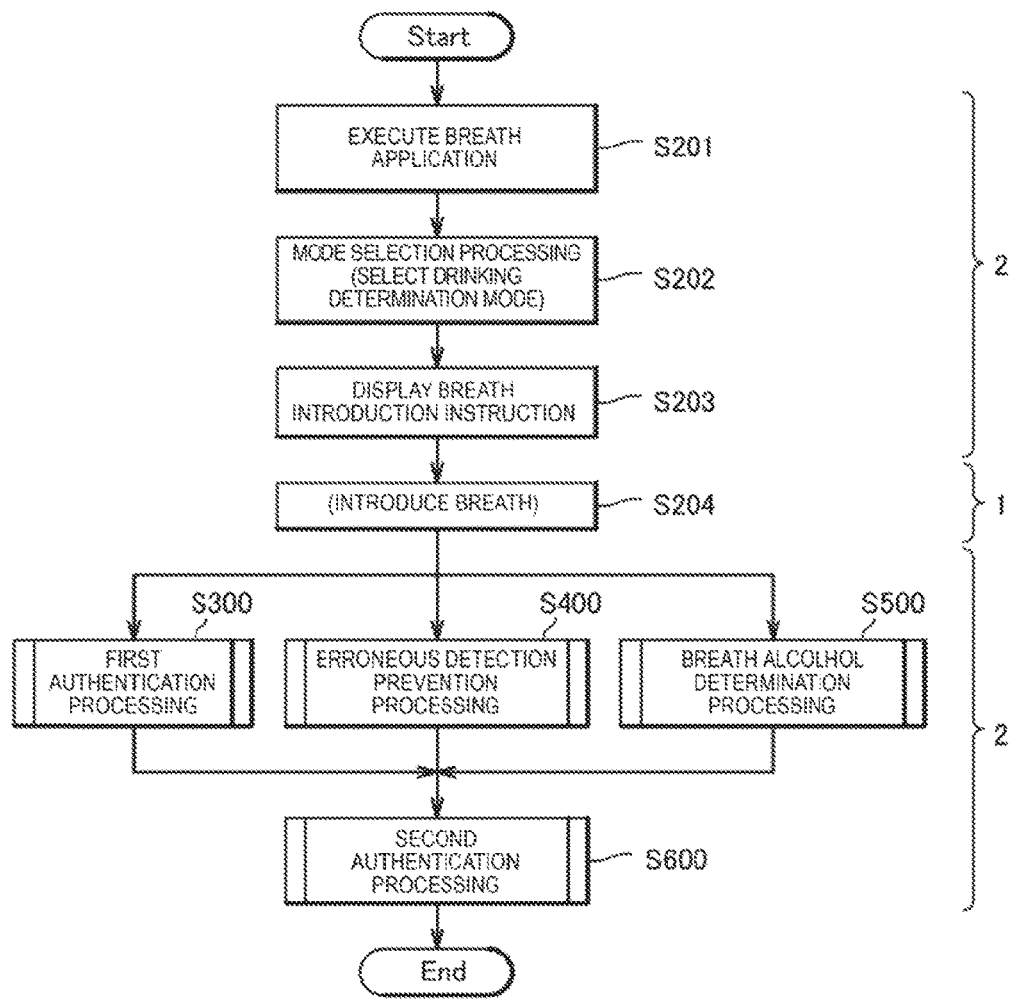

[Fig. 12]
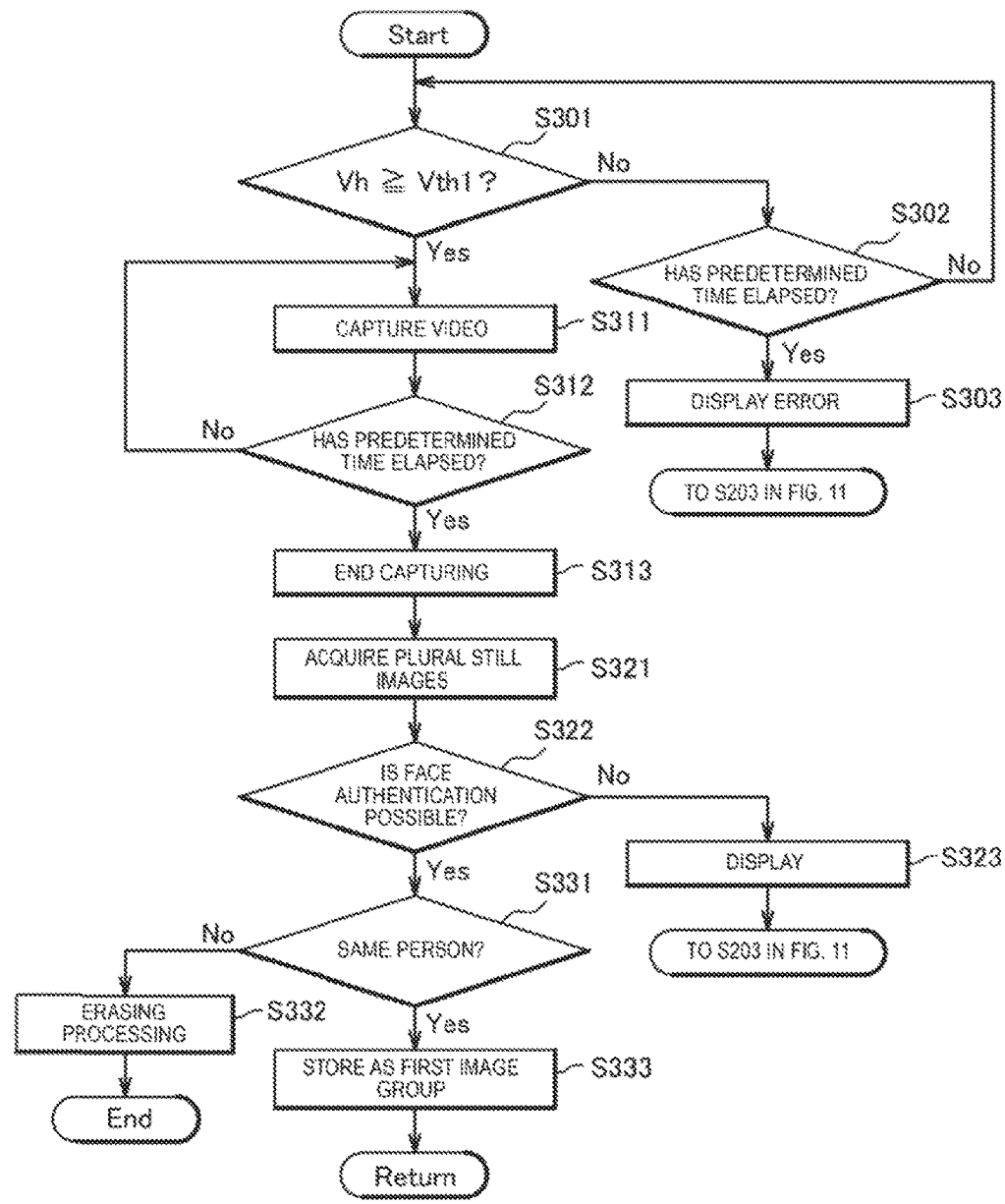

[Fig. 13]
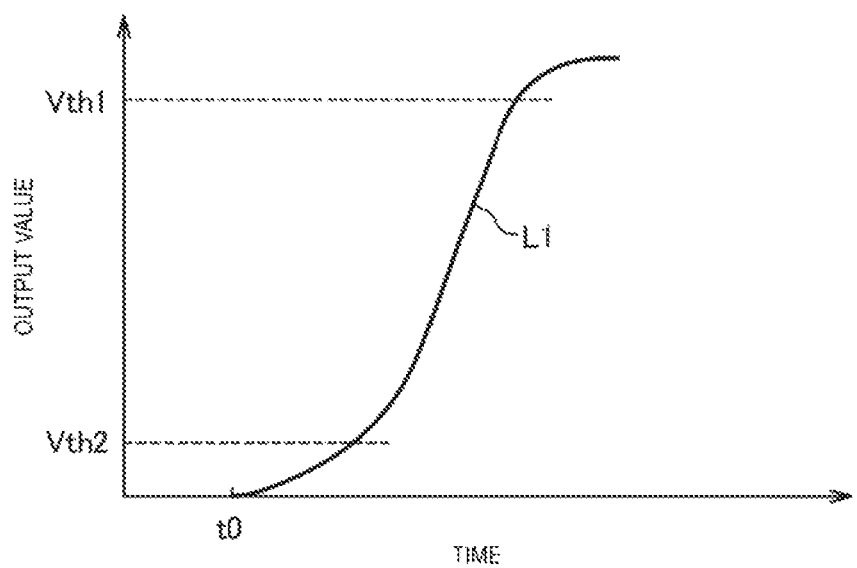

[Fig. 14]
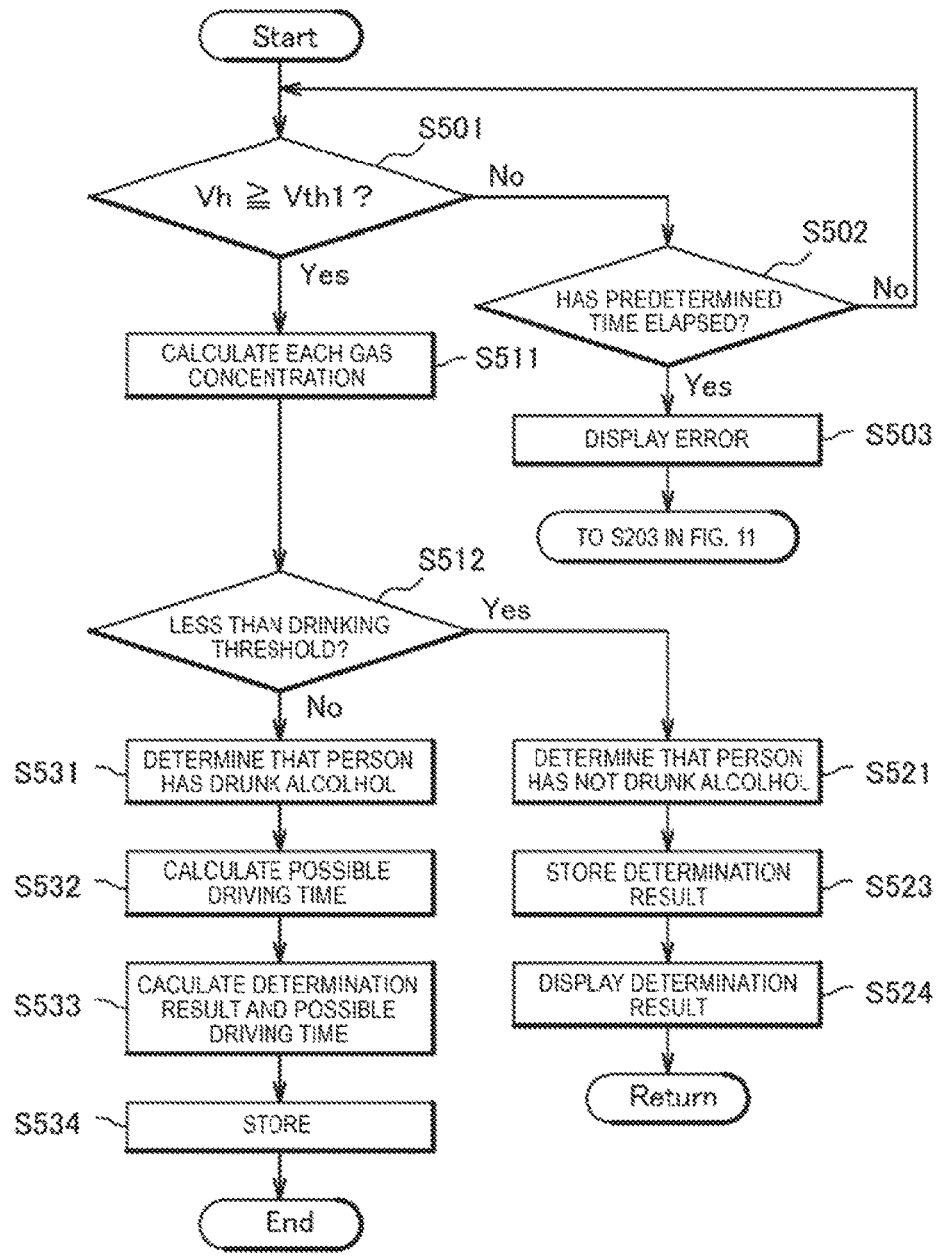

[Fig. 15]
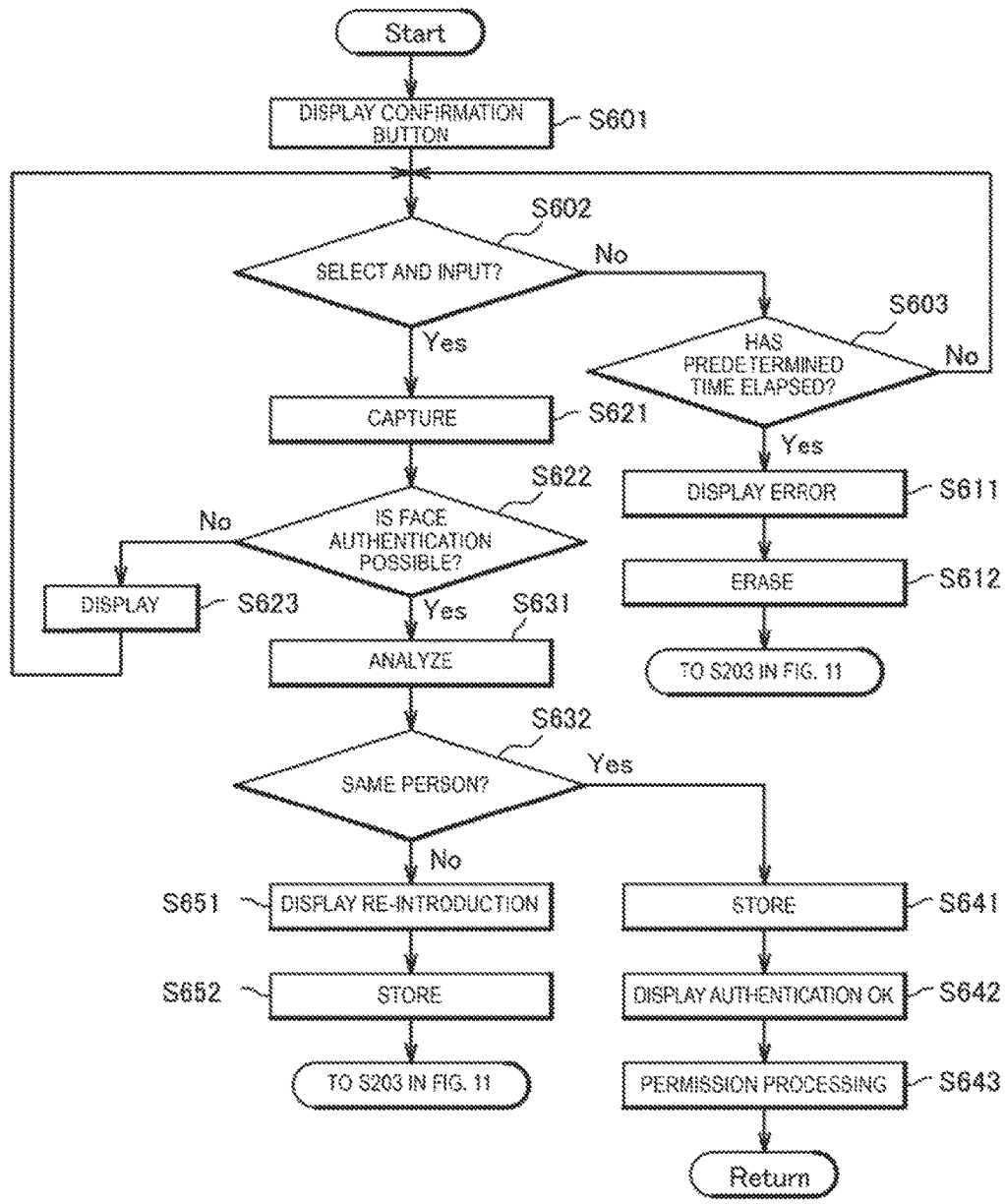

[Fig. 16]
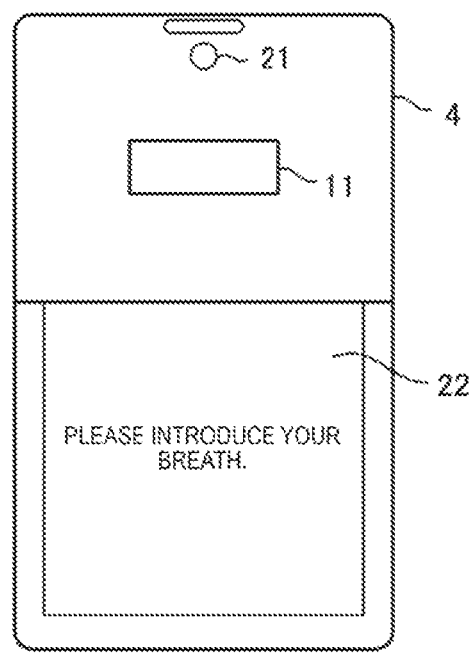

[Fig. 17]
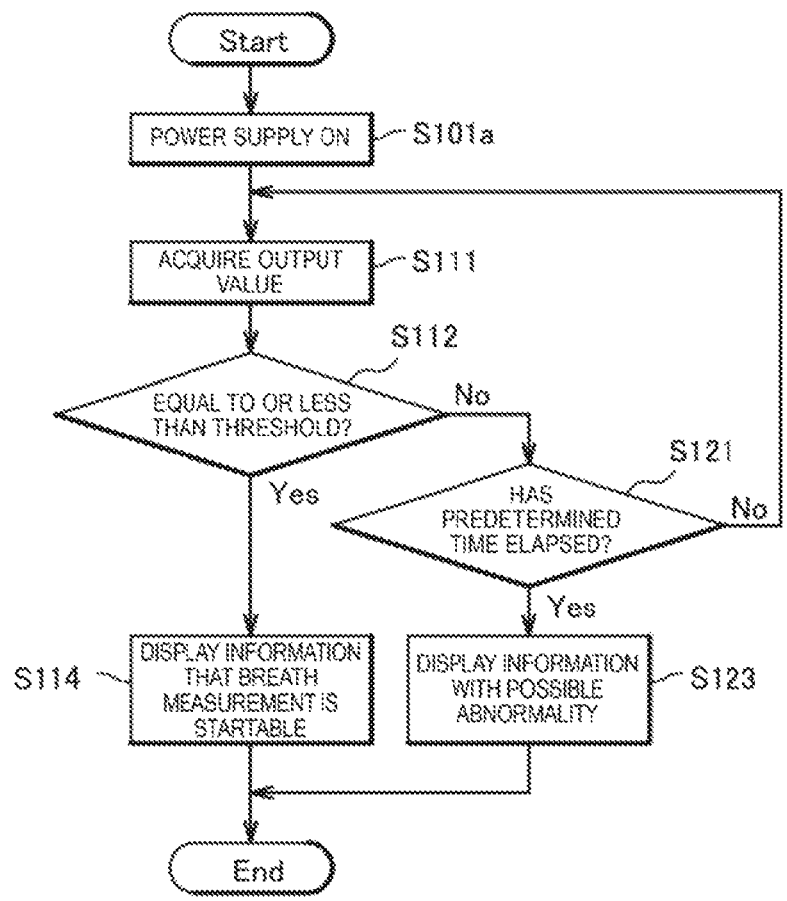

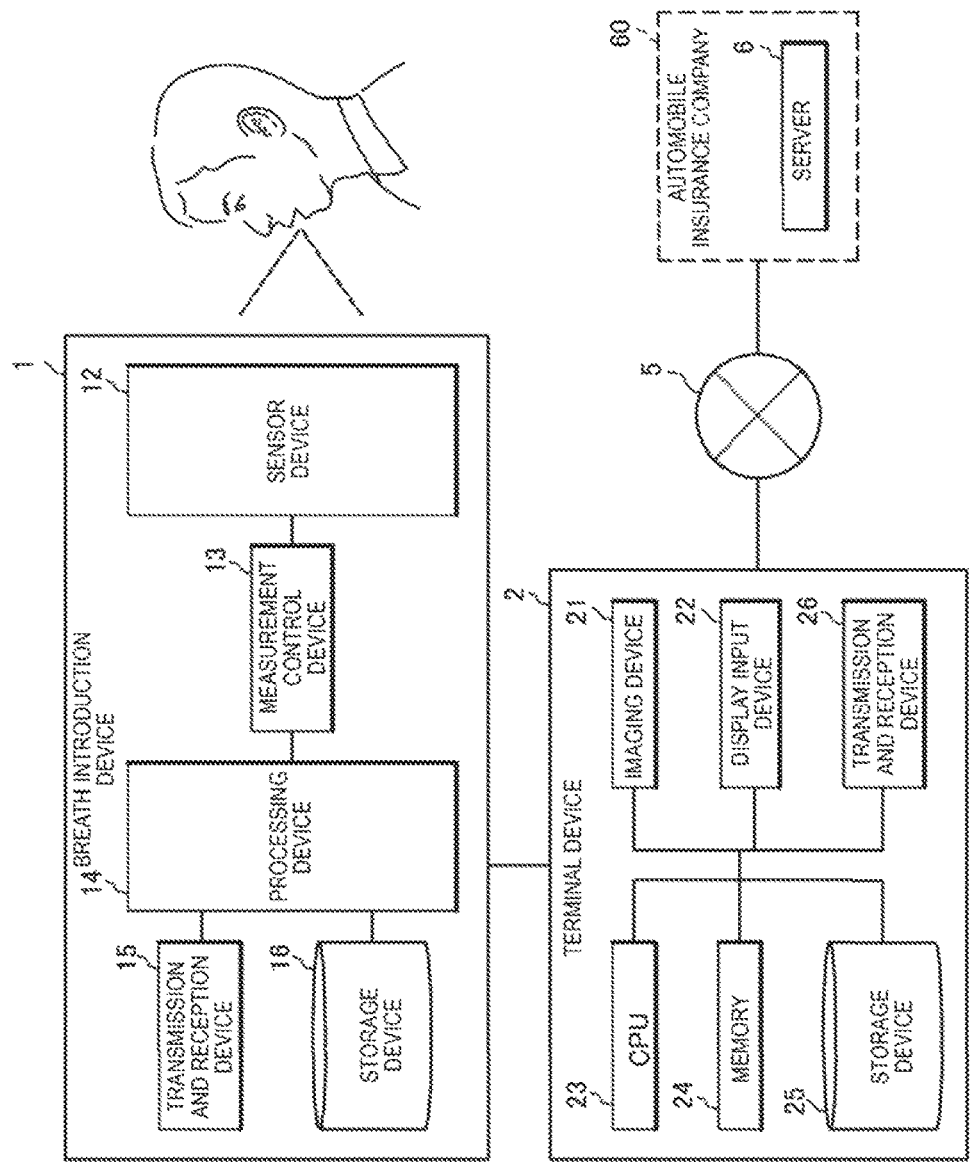
[Fig. 18]

[Fig. 19]
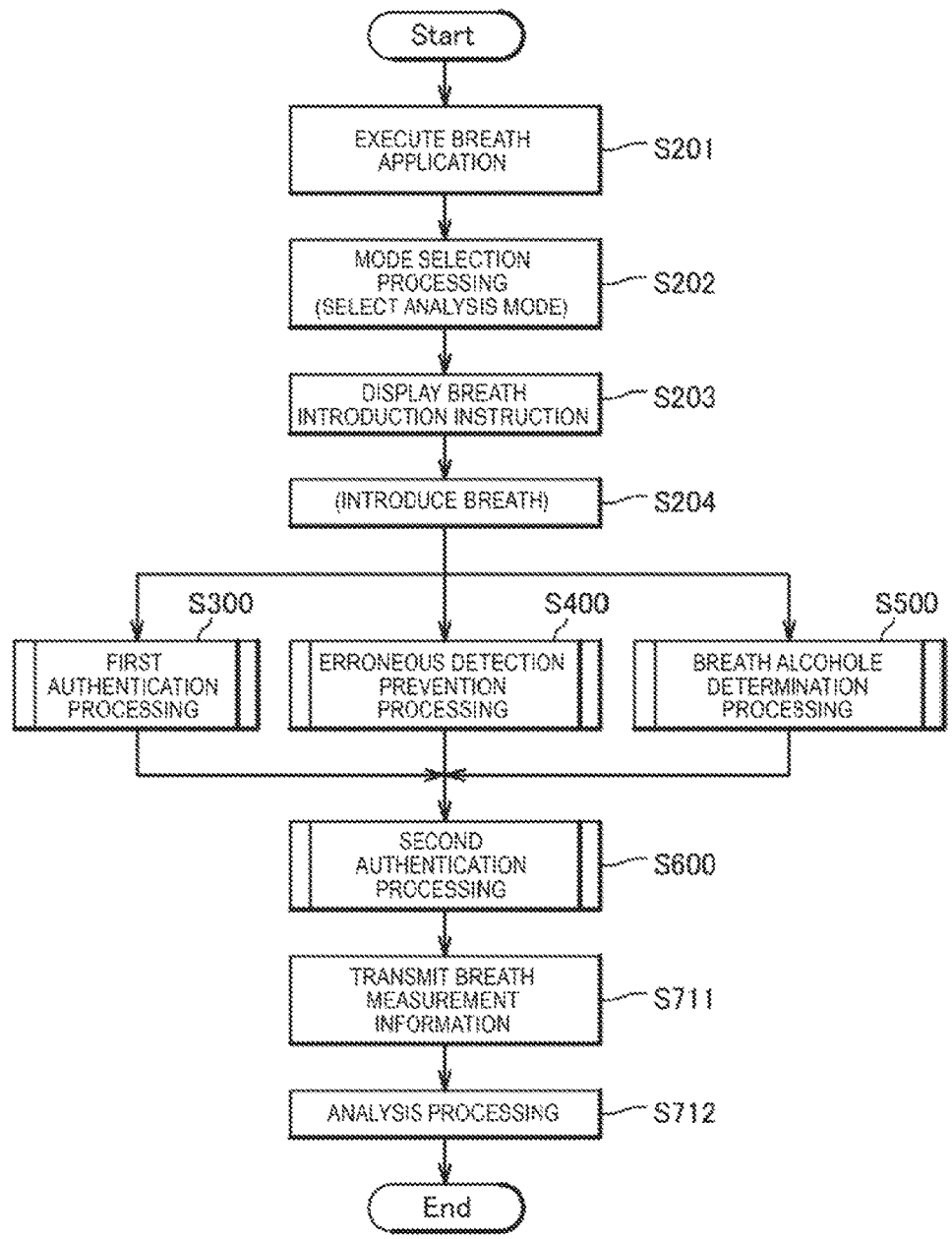

[Fig. 21]
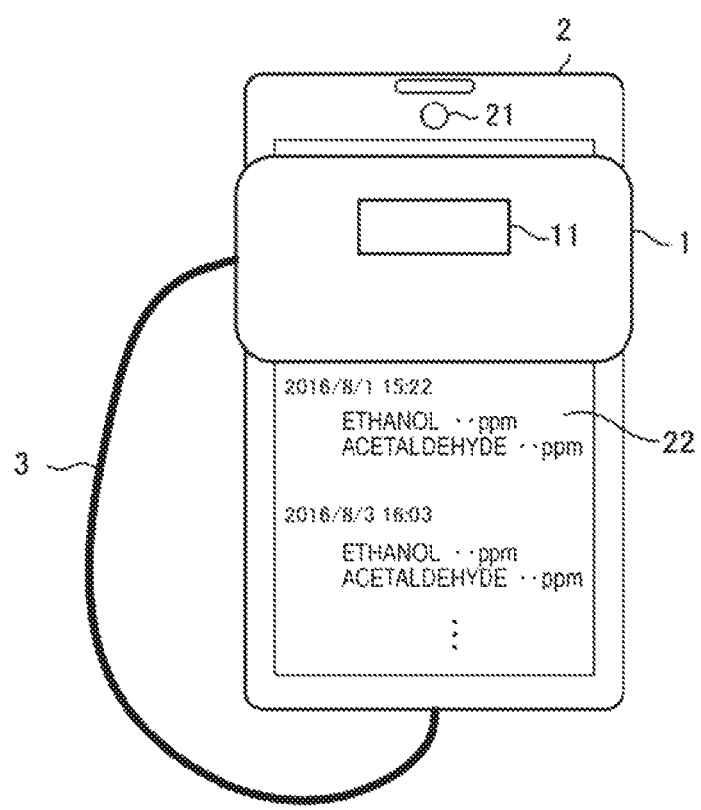

AUTHENTICATION SYSTEM AND AUTHENTICATION METHOD FOR DETECTING BREATH ALCOHOL

TECHNICAL FIELD

The present invention relates to a technology of an authentication system and an authentication method for preventing impersonation of a person introducing outside air.

BACKGROUND ART

As automatic operation of vehicles is considered to be practical in the future, it is predicted that drinking determination, detection of drivers' condition, and the like are increasingly important when the drivers switch between automatic operation and manual operation. When detecting alcohol concentration in drivers' breath for determining whether or not they have drunk alcohol, technologies for detecting a human's natural breath or preventing impersonation of drunken drivers are desired. In addition, there is an increasing need for mobile type detection terminals suitable for various use cases in the market, and it is necessary to respond to mobility of the terminals in the future.

In PTL 1, a driver monitoring device including "an interlock device for prohibiting the starting of an engine in a case where a camera capturing a driver and an alcohol detection device are provided, and alcohol is detected from the driver's breath by the alcohol detection device, in which the interlock device includes a step of capturing an image a plurality of times by the camera at different timings just before or just after alcohol detection operation by the alcohol detection device, a step of starting personal authentication based on artificial operation and performing personal authentication based on a plurality of captured images obtained by the camera, and a step of permitting the starting of the engine by a positive result of the person authentication" is disclosed.

CITATION LIST

Patent Literature

PTL 1: JP-A-2009-255864

SUMMARY OF INVENTION

Technical Problem

In the technology described in PTL 1, in order to ensure that alcohol detection is being performed by using breath of drivers themselves, an alcohol detector installed in an automobile and an in-automobile camera are used for drinking determination. However, in order to improve the convenience for a driver, in addition to a technology capable of determining who the person that measures his or her breath is (whether or not there is impersonation), a technology capable of determining whether the driver has drunk or not before the driver gets in an automobile by using a portable terminal is required. A technology capable of achieving these purposes at the same time has not been disclosed.

In addition, in PTL 1, a technology of authenticating an individual in the driver's seat by comparing two types of images including one image at the time of breath introduction (open mouth) for alcohol detection operation and the other image just before the alcohol detection operation (sober face) with images during driving is disclosed. However, since there is no mechanism to authenticate before the driver gets in an automobile with the data measured outside the automobile using a portable terminal device, in a case where it is determined that the driver must not drive after the driver has got in the automobile, it is necessary for the driver to wait without driving.

The present invention has been made in view of such a background, and an object of the present invention is to prevent impersonation in breath measurement by using a portable device.

Solution to Problem

In order to solve the above-mentioned problems, the present invention includes a breath introduction unit that breath of a person is introduced into, an imaging unit that captures images of the face of a person blowing breath on the breath introduction unit, a breath detection unit that detects components of the breath containing an alcohol component contained in the introduced breath from the breath introduction unit, an imaging control unit that controls the imaging unit, a breath analysis unit that analyzes the alcohol component of the breath detected by the breath detection unit, an image analysis unit that analyzes the images captured by the imaging unit, wherein the imaging control unit has a function of controlling the imaging unit to perform first image capturing during the introduction of the breath in the breath introduction unit and second image capturing after an analysis of the breath components in the breath analysis unit, the image analysis unit has a function of outputting a result as to whether or not a person of the images in the first image capturing and a person of the image in the second image capturing are the same person, and the breath introduction unit and the breath detection unit are configured to be mounted on a portable terminal accommodated in a portable housing and provided with the imaging unit or accommodated in the same housing as the portable terminal provided with the imaging unit. Other means for solving the problems will be described in an embodiment.

Advantageous Effects of Invention

According to the present invention, it is possible to prevent impersonation in breath measurement by using a portable device.

BRIEF DESCRIPTION OF DRAWINGS

FIG. 1 is an external view of a breath introduction device and a terminal device used in a first embodiment.

FIG. 2 is a diagram schematically showing first authentication processing used in the first embodiment.

FIG. 3 is a diagram schematically showing second authentication processing used in the first embodiment (part 1).

FIG. 4 is a diagram schematically showing second authentication processing used in the first embodiment (part 2).

FIG. 5 is a diagram showing the distance between an imaging device and a breath introduction inlet used in the first embodiment.

FIG. 6 is a diagram showing a hardware configuration of a breath introduction device and the terminal device used in the first embodiment.

FIG. 7 is a diagram showing a detailed hardware configuration of the breath introduction device.

FIG. 8 is a software functional block diagram of a breath introduction device used in the first embodiment.

FIG. 9 is a software functional block diagram of the terminal device used in the first embodiment.

FIG. 10 is a flowchart showing a procedure of initial processing used in the first embodiment.

FIG. 11 is a flowchart showing a procedure of entire breath measurement processing used in the first embodiment.

FIG. 12 is a flowchart showing a detailed procedure of the first authentication processing.

FIG. 13 is a diagram showing the temporal change of an output value of a water vapor sensor.

FIG. 14 is a flowchart showing a detailed procedure of breath alcohol determination processing.

FIG. 15 is a flowchart showing a detailed procedure of second authentication processing.

FIG. 16 is a diagram showing an external view of a breath analysis device used in a second embodiment.

FIG. 17 is a flowchart showing a procedure of initial processing used in the second embodiment.

FIG. 18 is a diagram showing a configuration of a breath analysis system used in a third embodiment.

FIG. 19 is a flowchart showing a procedure of entire breath measurement processing used in the third embodiment.

FIG. 20 is a diagram showing an example of analysis processing and analysis result performed in a server.

FIG. 21 is a diagram showing an example of historical information used in the third embodiment.

FIG. 22 is a diagram showing an example of a structure of a water vapor sensor according to the present embodiment.

FIG. 23 is a diagram describing the principle by which the water vapor sensor detects saturated water vapor according to the present embodiment.

DESCRIPTION OF EMBODIMENTS

Figure 5A:
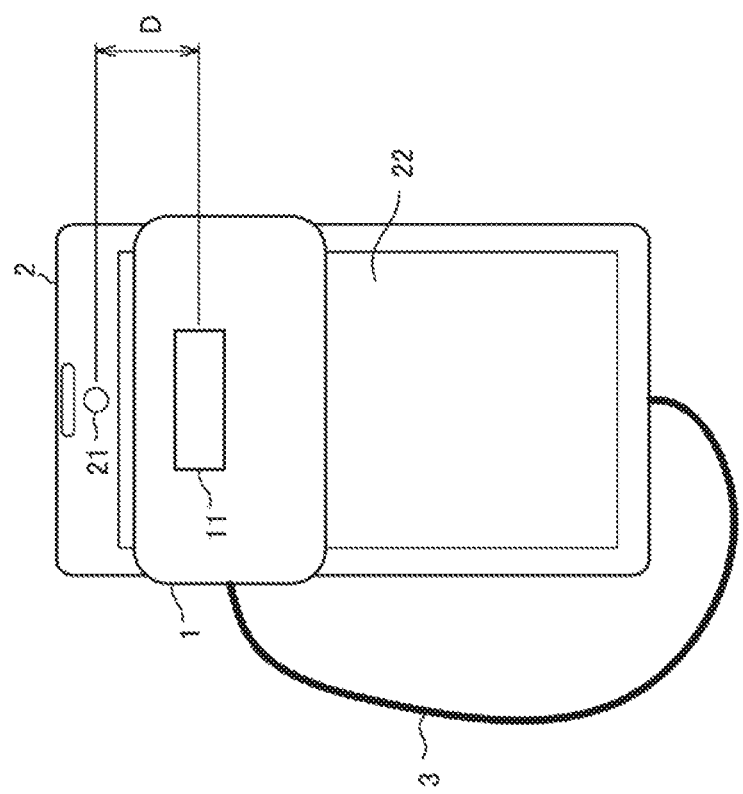
FIG. 5A is a diagram showing the definition of the distance between the imaging device and the breath introduction inlet.

Next, a form for implementing the present invention (referred to as an "embodiment") will be described in detail with reference to the appropriate drawings. In addition, in each drawing, the same components are denoted by the same reference numerals, and the description thereof will be omitted.

First Embodiment

First, a first embodiment of the present invention will be described with reference to FIGS. 1 to 15.

(Breath Introduction Device 1+Terminal Device 2)

FIG. 1 is an external view of a breath introduction device 1 and a terminal device 2 used in the first embodiment. Here, the terminal device (authentication system, portable terminal) 2 is a portable device such as a smartphone, a tablet terminal, or the like. The terminal device 2 is provided with an imaging device (imaging unit) 21 and a display input device (display unit) 22 which is a touch panel, and processes information transmitted from the breath introduction device 1 through a cable 3. Details of the terminal device 2 will be described later. The breath introduction device (outside air introduction device, authentication system) 1 is connected to the terminal device 2 via the cable 3 and is provided with a breath introduction inlet (outside air introduction unit) 11 into which breath (outside air) is introduced. In addition, the breath introduction device 1 is provided with various sensors as will be described later. Details of the breath introduction device 1 will be described later. The imaging device 21 is provided in the same direction as the breath introduction inlet 11. That is, the imaging device 21 is provided in the direction of the breath introduction inlet 11. The cable 3 is a Universal Serial Bus (USB) cable or the like.

Then, as shown in FIG. 1, the breath introduction device 1 is mounted on the terminal device 2. The breath introduction device 1 may be mounted on the terminal device 2 by being mounted from the side direction of the terminal device 2, mounted from the front side (the side where the display input device 22 is) or mounted from the upward direction, and the way of being mounted does not matter. In addition, the breath introduction device 1 may be installed in the terminal device 2 by providing an adhesive portion at a part facing the terminal device 2 of the breath introduction device 1 and attaching the breath introduction device 1 to the terminal device 2. However, the imaging device 21 of the terminal device 2 and the breath introduction inlet 11 are installed in a way that the distance thereof is within a predetermined distance as will be described later. In addition, the breath introduction device 1 may be mounted so as to extend from the terminal device 2.

<First Authentication Processing>

FIG. 2 is a diagram schematically showing the first authentication processing used in the first embodiment. In the present embodiment, two-step authentication is performed in the first authentication processing shown in FIG. 2 and the second authentication processing which will be described later. FIG. 1 will be referred to as appropriate. In FIG. 2, the distance between the breath introduction device 1 and the terminal device 2, and the user is shown in the middle part, and examples of images captured by the imaging device 21 of the terminal device 2 are shown in the upper part and the lower part. An example of an image of authentication OK is shown in the upper row, and an image example of authentication NG is shown in the lower row. "T0" to "T3" shown in FIG. 2 indicate time, and the time advances in the order of "T0"→"T1"→"T2"→"T3". The time "T0" is the time at which introduction of breath is started. At the time "T1", breath introduction has ended. In addition, a reference symbol A shown in the middle part of FIG. 2 shows an imaging range of the imaging device 21.

A case of authentication OK will be described with reference to the upper part and middle part of FIG. 2. With the breath introduction being performed from the breath introduction inlet 11 of the breath introduction device 1 as a trigger, the imaging device 21 of the terminal device 2 performs image capturing at the time "T0". At this time, a user brings his or her face (mouth) close to the breath introduction inlet 11 of the breath introduction device 1. Therefore, the user is also bringing his or her face to the terminal device 2 mounted on the breath introduction device 1. Therefore, in an image P10 captured at the time "T0", the user's mouth area is captured. In addition, since the user is performing breath introduction at the time "T0", the user's mouth is in the state of being open in the image P10.

The terminal device 2 continues to capture images for a predetermined time with the breath introduction being performed from the breath introduction inlet 11 of the breath introduction device 1 as a trigger (first capturing). The continuous image capturing for a predetermined time may be video capturing or still images capturing (frame capturing) at predetermined intervals. The images at times "T1", "T2", and "T3" captured in this manner are shown as images P11 to P13. As described above, the still images captured at the respective timings "T1", "T2", and "T3" may be the images P11 to P13, or the still images corresponding to the respective timings "T1", "T2", and "T3" may be extracted from the video to generate the images P11 to P13. The images P10 to P13 are referred to as a first image group. Here, it is assumed that still images are extracted from the video. By extracting still images from the video, it is possible to acquire still images having a shorter time interval between the images than images acquired by continuous capturing of still images, and it is possible to improve the accuracy of authentication.

As described above, since the breath introduction has already been ended at time "T1", the mouth is in a state of being closed in the image P11 (breath analysis is not performed at this time). In addition, as shown in the middle part of FIG. 2, since the breath introduction is ended, the user gradually moves the breath introduction device 1 and the terminal device 2 away from the face over the time "T1" to "T3". Therefore, the range of the face being captured increases over the images P11 to P13. The terminal device 2 determines whether or not all the persons captured in the images P10 to P13 are the same person, based on the feature amounts and the like around the mouth in the images P10 to P13. Since the persons captured in the images P10 to P13 shown in the upper part of FIG. 2 are the same person, the terminal device 2 makes a determination of authentication OK.

On the other hand, in the example shown in the lower part of FIG. 2, the same person is shown in the images P10 and P11, but at the time "T2", an image P22 with nothing captured is acquired. Further, in an image P23 at the time "T3", a person different from the persons captured in the images P10 and P11 is captured. In such a case, the terminal device 2 makes a determination of authentication NG.

In this way, by comparing the image P10 in which breath is being introduced and the images P11 to P13 continuously captured from the introduction of breath, it is possible to determine whether or not the persons are changed from the person captured in the image P10 in which breath is being introduced.

In addition, in the present embodiment, if all the images P10 to P13 in FIG. 2 are the same person, a determination of OK is made in a first authentication. On the other hand, if at least the image P10 (the image at breath introduction) and the image P13 (the image last captured in the first image group) are the same person, a determination of OK is made in the first authentication.

In addition, the image P10 shown in FIG. 2 is an image in which the mouth area is captured, but this indicates that the breath introduction inlet 11 is close to the mouth of the user, and the image P10 is an image unique to the portable terminal device 2. In this way, for example, it is possible to prevent breath introduction using other appliances or the like by pretending to introduce breath in the mouth. In FIG. 2, four images are captured, but the number of images is not limited to four.

<Second Authentication Processing>

FIGS. 3 and 4 are diagrams schematically showing the second authentication processing used in the first embodiment. In FIG. 3, the same components as in FIG. 1 are denoted by the same reference numerals, and the description thereof will be omitted. In the first authentication processing, if the terminal device 2 makes a determination of authentication OK and the alcohol concentration of breath introduced from the breath introduction inlet 11 is less than a predetermined threshold, as shown in FIG. 3, the terminal device 2 displays a confirmation button (symbol) B together with a determination of breath alcohol concentration (drinking determination: OK) or information on breath volume introduced (breath volume: OK) on the display input device 22.

When the user selects and inputs the confirmation button B displayed on the display input device 22 of the terminal device 2, a still image is captured by the imaging device 21.

An image P30 shown in FIG. 4 is an image (second image) captured when the confirmation button B is selected and input. That is, the image P30 is captured at a time different from the image P13 in FIG. 2. The terminal device 2 compares all of the images P10 to P13 acquired at the time of the first authentication processing with the image P30 captured at the time of selection and input of the confirmation button B, and determines whether or not the persons captured in the images P10 to P13 and the image P30 are the same person from the feature points of the face. In a case of the same person, the terminal device 2 performs processing such as unlocking the key of an automobile. In addition, in this case, according to the drinking determination, the terminal device 2 and the automobile may operate in conjunction with each other. By determining whether or not the persons captured in the image P10 in which breath is being introduced, the images P11 to P13, and the image P30 are the same person, after analyzing the breath components (after determining drinking), it is possible to determine whether or not the person who selects and inputs the confirmation button B is the person who introduced the breath. The person in one of the images P10 to P13 acquired in the first authentication processing (at least the image P10 at breath introduction and the image P13 which is the last image of the first image group) and the person in the image P30 captured at the time the confirmation button B is selected and input are the same person, it may be determined as OK in the second authentication processing.

<Distance Between Imaging Device 21 and Breath Introduction Inlet 11>

Figure 5B:
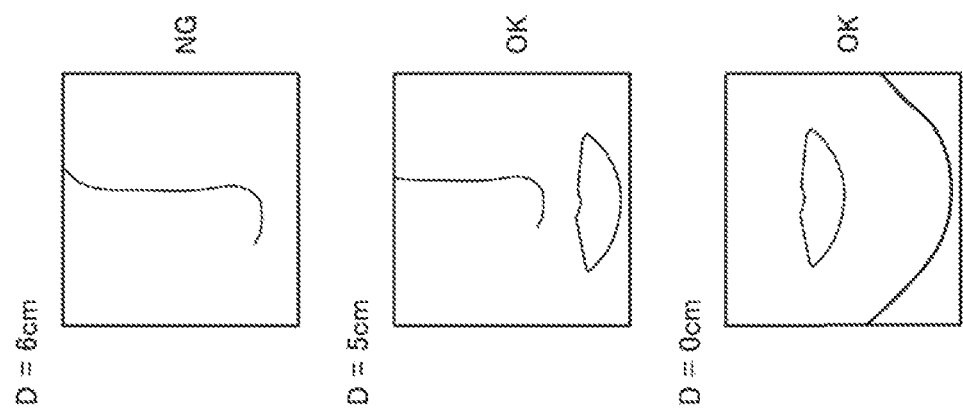
FIG. 5B is a diagram showing an image in each distance between the imaging device and the breath introduction inlet.

FIG. 5 shows the distance between the imaging device 21 and the breath introduction inlet 11 used in the first embodiment, FIG. 5A shows the definition of the distance between the imaging device 21 and the breath introduction inlet 11, and FIG. 5B shows an image for each distance between the imaging device 21 and the breath introduction inlet 11. In the image captured at the time of breath introduction (the image captured at the time "T0" in FIG. 2), at least the mouth is captured. In this way, by capturing the mouth in the image captured at breath introduction, it is possible to determine whether or not breath introduction is actually performed. As shown in FIG. 5A, when the distance between the imaging device 21 and the center of the breath introduction inlet 11 is D, as shown in FIG. 5B, the mouth is captured until D=0 to 5 cm, but all of the mouth is not captured in D=6 cm. Therefore, the distance between the imaging device 21 (lens) and the center of the breath introduction inlet 11 is preferably 0 to 5 cm. D=0 means that the imaging device 21 is in a state of being installed at the center of the breath introduction inlet 11, for example, the breath introduction inlet 11 is composed of a transparent member, and the imaging device 21 is in a state of being installed on the back of the transparent member.

<Hardware Configuration>

FIG. 6 is a diagram showing a hardware configuration of a breath introduction device 1 and the terminal device 2 used in the first embodiment. The breath introduction device 1 includes a sensor device (detection unit) 12, a measurement control device 13, a processing unit 14, a transmission and reception device 15, and a storage device 16. The sensor device 12 is provided with various sensors and sends a detection signal regarding gases and the like contained in breath introduced from the breath introduction inlet 11 (see FIG. 1) to the measurement control device 13. The sensor device 12 will be described later.

The measurement control device 13 supplies the power of the breath introduction device 1, generates necessary signals to the sensor device 12, amplifies the detection signals of the sensor device 12, and sends the signals to the processing unit 14. The measurement control device 13 will be described later. The processing unit 14 acquires the output of each of the sensors 121 to 127 (see FIG. 7) of the sensor device 12 acquired via the measurement control device 13, and performs processing as necessary. The processing unit 14 will be described later. The transmission and reception device 15 transmits the output value of each of the sensors 121 to 127 of the sensor device 12, the processing result of the processing unit 14, or the like to the terminal device 2 via the cable 3 (see FIG. 1). The storage device 16 stores the output value of each of the sensors 121 to 127 of the sensor device 12, the processing result of the processing unit 14, or the like.

The terminal device 2 includes the imaging device 21, the display input device 22, a Central Processing Unit (CPU) 23, a memory 24, a storage device 25, and the transmission and reception device 26. The programs stored in the storage device 25 are loaded into the memory 24 which is a main storage device, and are executed by the CPU 23, whereby each of the units 200 to 209 (see FIG. 9) which will be described later is implemented. The storage device 25 is a Read Only Memory (ROM) or the like, and stores the programs executed in the memory 24, the results processed by each of the units 200 to 209, or the like.

Although it is desirable that the imaging device 21 is a camera, and both still image capturing and video capturing are performed, but only still image capturing may be performed. The display input device 22 is a touch panel and has input and display functions. The transmission and reception device 26 acquires information from the breath introduction device 1 via the cable 3, and performs transmission and reception with the server 6 which will be described later.

FIG. 7 is a diagram showing a detailed hardware configuration of the breath introduction device 1.

In FIG. 7, the sensor device 12, the measurement control device 13, and the processing unit 14 will be described. The sensor device 12 includes a gas sensor device 120 having a hydrogen sensor (detection element) 121, a water vapor sensor (saturated water vapor detection element) 122, an acetaldehyde sensor (detection element) 123, an alcohol sensor (detection element) 124, and a bad breath sensor 125, a temperature sensor 126, and a humidity sensor 127. The hydrogen sensor 121 detects the hydrogen level in breath. A water vapor sensor 122 detects whether or not the introduced outside air (breath) is saturated water vapor and has a sufficient introduction volume for calculation of each gas concentration (particularly ethanol concentration) contained in the breath. An acetaldehyde sensor 123 detects the acetaldehyde level in breath. The alcohol sensor 124 detects the alcohol (ethanol) level in breath.

The bad breath sensor 125 detects methyl mercaptan, hydrogen sulfide, dimethyl sulfide, and the like which cause bad breath. By providing a bad breath sensor 125, it can help the user to use the breath introduction device 1 on a daily basis. The temperature sensor 126 measures temperature. The humidity sensor 127 measures humidity. The temperature sensor 126 and the humidity sensor 127 are used for changing a threshold of the water vapor sensor 122, which will be described later, according to the use environment condition of the breath introduction device 1. That is, the threshold of the water vapor sensor 122 which will be described later may be changed according to temperature and humidity. Thus, it is possible to determine the correct breath introduction volume. The bad breath sensor 125 will be omitted.

The measurement control device 13 includes a CPU 131, a power supply 132, an amplifier 133, and a signal generation device 134. The power supply 132 supplies electric power for driving the sensor device 12, the measurement control device 13, and the processing unit 14. If power can be acquired from the terminal device 2 with a USB cable or the like, the power supply 132 may be omitted. The amplifier 133 amplifies the signals from the sensors 121 to 127 of the sensor device 12. The signal generation device 134 converts the voltage of the power supply 132 to an AC voltage necessary for the water vapor sensor 122. The water vapor sensor 122 and the AC voltage will be described later.

The processing unit 14 includes a CPU 141, a memory 142, and an Analog/Digital (A/D) converter 143. The A/D converter 143 converts analog signals of the sensors 121 to 127 amplified via the amplifier 133 into digital signals. Then, various programs of the memory 142 are executed by the CPU 141 so that each of the units 100 to 102 (see FIG. 8) which will be described later is implemented.

<Software Functional Block Diagram>

FIG. 8 is a software functional block diagram of a breath introduction device 1 used in the first embodiment. The breath introduction device 1 includes a processing unit 100. The processing unit 100 includes a determination unit 101 and a transmission processing unit 102. Details of the processing in each of the units 100 to 102 will be described later. The determination unit 101 determines whether or not the output value of each of the sensors 121 to 127 in the sensor device 12 are normal. The transmission processing unit 102 transmits the output value of each of the sensors 121 to 127, the determination result by the determination unit 101, and the like to the terminal device 2 (see FIG. 1). As described above, each of the units 100 to 102 in FIG. 8 is implemented by executing various programs of the memory 142 in the processing unit 14 of FIG. 7 by the CPU 141.

FIG. 9 is a software functional block diagram of the terminal device 2 used in the first embodiment. The terminal device 2 includes the processing unit 200. The processing unit 200 includes an output value acquisition unit 201, a water vapor sensor output processing unit 202, a display processing unit 203, a gas concentration calculation processing unit (concentration calculation unit) 204, an imaging processing unit 205, an drinking determination processing unit (first analysis unit) 206, a first authentication processing unit (authentication unit) 207, a possible driving time calculation unit 208, and a second authentication processing unit (authentication unit) 209. Details of processing in each of the units 200 to 209 will be described later.

The output value acquisition unit 201 acquires the output value of each of the sensors 121 to 127 (see FIG. 7) in the sensor device 12 from the breath introduction device 1 via the cable 3. The water vapor sensor output processing unit 202 makes a determination as to whether or not the output value detected by the water vapor sensor 122 is equal to or less than the predetermined threshold. The display processing unit 203 causes the display input device 22 (see FIG. 6) to display. The gas concentration calculation processing unit 204 calculates the concentration of each gas contained in the breath based on the output value of each of the sensors 121 to 127. The imaging processing unit 205 causes the imaging device 21 to perform capturing.

The drinking determination processing unit 206 makes a drinking determination based on the alcohol concentration and the like in the breath calculated by the gas concentration calculation processing unit 204. The first authentication processing unit 207 performs the first authentication processing. In a case where it is determined that the user has drunk alcohol by the drinking determination processing unit 206, the possible driving time calculation unit 208 calculates the time until the blood alcohol concentration falls to the extent that the user can drive, based on the alcohol concentration and the like in the breath calculated by the gas concentration calculation processing unit 204. The second authentication processing unit 209 performs the second authentication processing. As described above, the program stored in the storage device 25 is loaded into the memory 24 of FIG. 6, and the loaded program is executed by the CPU 23 so that each of the units 200 to 209 is implemented.

<Flowchart>

Next, with reference to FIGS. 10 to 15, the processing of the breath introduction device 1 and the terminal device 2 will be described. In FIGS. 10 to 15, FIG. 1 and FIGS. 6 to 9 will be referred to as appropriate.

(Initial Processing)

FIG. 10 is a flowchart showing a procedure of initial processing used in the first embodiment. Here, the initial processing is performed when the breath introduction device 1 is powered on. First, the breath introduction device 1 and the terminal device 2 are connected by the cable 3 by the user (S101). The breath introduction device 1 and the terminal device 2 are connected with the cable 3, whereby the breath introduction device 1 is powered on (S102). In this way, it is possible to prevent forgetting to power the breath introduction device 1 on. Then, initialization processing of the sensors 121 to 127 shown below is executed.

The output value acquisition unit 201 of the breath introduction device 1 (processing unit 100 thereof) acquires the output value of each of the sensors 121 to 127 provided in the breath introduction device 1 (S111). Next, the determination unit 101 of the breath introduction device 1 (processing unit 100 thereof) determines whether or not all of the acquired output values of the sensors 121 to 127 are equal to or less than the predetermined threshold (S112). As a result of step S112, in a case where all of the acquired output values of the sensors 121 to 127 are equal to or less than the predetermined threshold (S112→Yes), the transmission processing unit 102 of the breath introduction device 1 transmits information (normal information) indicating that all of the output values of the sensors 121 to 127 are equal to or less than the predetermined threshold value to the terminal device 2 (S113). Since the sensors 121 to 127 are operating normally, the display processing unit 203 of the terminal device 2 displays information (information of startable breath measurement) indicating that breath measurement can be started on the display input device 22 (S114).

As a result of step S112, in a case where any of the acquired output values of the sensors 121 to 127 is larger than the predetermined threshold (S112→No), the determination unit 101 of the breath introduction device 1 determines whether or not the predetermined time has elapsed since the power is on in step S102 (S121). As a result of step S121, in a case where the predetermined time has not elapsed (S121→No), the processing unit 100 of the breath introduction device 1 returns the processing to step S111. In a case where the predetermined time has elapsed as a result of step S121 (S121 Yes), the transmission processing unit 102 of the breath introduction device 1 transmits information (abnormal information) indicating that there is a sensor showing an abnormal value to the terminal device 2 (S122). The display processing unit 203 of the terminal device 2 displays information (information of possible abnormality) indicating that there is a possibility that a sensor abnormality may occur on the display input device 22 (S123).

In the present embodiment, a determination (S122) is made in the breath introduction device 1 as to whether or not all of the output values of the sensors 121 to 127 are equal to or less than the predetermined threshold, but the determination may be made in the terminal device 2.

(Entire Breath Measurement Processing)

FIG. 11 is a flowchart showing a procedure of entire breath measurement processing used in the first embodiment. Because the sensors 121 to 127 are normally operating at step S113 in FIG. 10, the user who confirms that the breath measurement can be started is instructed to execute the breath measurement application (S201) so that each of the units 200 to 209 shown in FIG. 9 is activated. Next, the user operates the terminal device 2 to select either a drinking determination mode or an analysis mode (mode selection processing: S202). Here, it is assumed that the drinking determination mode is selected. In the terminal device 2, when all of the units 200 to 209 are activated, the display processing unit 203 of the terminal device 2 displays information (breath introduction instruction) prompting breath introduction on the display input device 22 (S203). The user who has confirmed that information prompting breath introduction is displayed introduces breath from the breath introduction inlet 11 of the breath introduction device 1 (S204). In other words, the user brings the mouth close to the breath introduction inlet 11 and blows breath. Thereafter, the terminal device 2 performs the first authentication processing (S300), the erroneous detection prevention processing (S400), and the breath alcohol determination processing (S500) in parallel. Each processing of the first authentication processing (S300), the erroneous detection prevention processing (S400), and the breath alcohol determination processing (S500) will be described later.

When each processing of the first authentication processing (S300), the erroneous detection prevention processing (S400), and the breath alcohol determination processing (S500) is ended, the breath introduction device 1 and the terminal device 2 perform the second authentication processing (S600), and the breath measurement processing is ended. In the erroneous detection prevention processing, the processing unit 200 determines whether or not the output voltage of the hydrogen sensor 121, the water vapor sensor 122, the acetaldehyde sensor 123, and the alcohol sensor 124 after breath introduction exceeds a threshold. In this way, it is determined whether or not the outside air (gas) introduced to the breath introduction device 1 is human breath. Here, a detailed description of the erroneous detection prevention processing will be omitted.

(First Authentication Processing)

FIG. 12 is a flowchart showing a detailed procedure of the first authentication processing (S300) in FIG. 11. When breath is introduced at step S204 in FIG. 11, the water vapor sensor output processing unit 202 of the terminal device 2 determines whether or not an output value Vh of the water vapor sensor 122 is equal to or greater than a threshold Vth1 indicating that sufficient breath introduction is being performed (S301). Here, the threshold Vth1 indicating that sufficient breath introduction is being performed is used, but a threshold Vth2 indicating that breath introduction has started may be used.

Here, the threshold used in step S301 of FIG. 12 will be described with reference to FIG. 13. In FIG. 13, a vertical axis shows the output value of the water vapor sensor 122 and a horizontal axis shows time. If it is assumed that breath introduction starts at time t0, the output value of the water vapor sensor 122 rises as shown in a graph L1. As described above, since the water vapor sensor 122 detects whether or not the introduced outside air (breath) is saturated water vapor or not, the output value is "0" or "1". However, in reality, the output value does not rise instantaneously, as shown in FIG. 13, the output value rises over a predetermined period of time, although it is a very short time. Here, the threshold Vth2 is a threshold indicating that breath introduction has started. Since the influence of the noise of the water vapor sensor 122 is taken into consideration, a value larger than noise is the threshold Vth2. In addition, the threshold Vth1 is a threshold indicating that sufficient breath introduction is being performed. As described above, in step S301, the threshold Vth2 may be used, or the threshold Vth1 may be used.

In FIG. 13, it is assumed that the output of the water vapor sensor 122 is a DC, but in a case where the water vapor sensor 122 which will be described later in FIGS. 22 and 23 is used, the output of the water vapor sensor 122 is an AC. In this case, the graph of FIG. 13 is obtained by connecting the peak values of the AC voltage.

Description will be returned to FIG. 12. As a result of step S301, in a case where the output value Vh of the water vapor sensor 122 is less than the threshold Vth1 (S301→No), the water vapor sensor output processing unit 202 determines whether or not the predetermined time has elapsed since the breath introduction was performed (S302). As a result of step S302, in a case where the predetermined time has not elapsed since breath introduction was performed (S302 No), the water vapor sensor output processing unit 202 returns the processing to step S301. As a result of step S302, in a case where the predetermined time has elapsed since the breath introduction was performed (S302→Yes), the display processing unit 203 displays an error message such as "Because the introduction volume is insufficient, please measure again." or the like on the display input device 22 (S303). Thereafter, re-introduction of breath is performed by the processing unit 200 by returning to step S203 of FIG. 11.

As a result of step S301, in a case where the output value Vh of the water vapor sensor 122 is equal to or greater than the threshold Vth1 (S301→Yes), the imaging processing unit 205 performs video capturing (the first image capturing at the introduction of breath in the breath introduction inlet 11) by the imaging device 21 (S311). That is, the video capturing is started with the output value of the water vapor sensor 122 becoming equal to or greater than the threshold Vth1 as a trigger. Although the video capturing is used here, normal still images may be captured (frame capturing). As described above, with the output value of the water vapor sensor 122 becoming equal to or larger than the threshold Vth1 (or the threshold Vth2), it is possible to reliably capture an image under breath introduction by performing capturing in step S311. Thereafter, the imaging processing unit 205 determines whether or not a predetermined time has elapsed since the video capturing by the imaging device 21 started (S312). Here, the predetermined time is a time during which an image having a degree enough to make the determination at step S331 can be acquired. As a result of step S312, in a case where the predetermined time has not passed since the capturing by the imaging device 21 started (S312→No), the imaging processing unit 205 returns the processing to step S311 and continues the video capturing.

As a result of step S312, in a case where the predetermined time has elapsed since the capturing by the imaging device 21 started (S312→Yes), the imaging processing unit 205 ends the capturing in step S311 (S313), and the first authentication processing unit 207 acquires a plurality of still images at predetermined intervals from the captured video (S321). In a case where the still image capturing is being performed instead of the video capturing in step S311, the first authentication processing unit 207 acquires the number of still images necessary for the determination in step S331 from the captured still images. The still images acquired in step S321 are images corresponding to the images P10 to P13 in FIG. 2. Then, the first authentication processing unit 207 determines whether or not a plurality of still images acquired in step S321 can be subjected to face authentication (S322). Whether face authentication is possible or not depends on whether or the mouth is captured at least. In step S322, the first authentication processing unit 207 may determine whether or not breath introduction is correctly performed based on the shape of the mouth captured in a first piece of the acquired still image.

As a result of step S322, in a case where face authentication is impossible (S322→No), the display processing unit 203 causes the display input device 22 to display a message such as "Please introduce breath again." and the confirmation button B (see FIG. 3) (S323), and the processing returns to step S203 of FIG. 11. As a result of step S322, in a case where face authentication is possible (S322→Yes), the first authentication processing unit 207 determines whether or not all of the plurality of acquired still images are the images of the same person (S331).

In step S331, the first authentication processing unit 207 processes the following information as feature points.

(1) Position of a Specific Area of the Mouth

As shown in the images P11 to P13 in FIG. 2, as the imaging device 21 moves away from the user, in a case where a nose, eyes, eyebrows are captured, the positions of specific parts of the eyes and the eyebrows may be used as feature points.

(2) Position of the Edge Line of the Mouth

As shown in the images P11 to P13 in FIG. 2, as the imaging device 21 moves away from the user, in a case where a nose, eyes, eyebrows are captured, the positions of edge lines of the eyes and the eyebrows may be used as feature points.

(3) Skin Color

As a result of step S331, in a case where all of the plurality of acquired still images are not the images of the same person (S331→No), that is, in a case where images of different persons are mixed, the first authentication processing unit 207 performs erasure processing for erasing the plurality of acquired still images and video (S332). Then, the display processing unit 203 causes the display input device 22 to display an error message such as authentication failure, re-measurement instruction or the like, and the processing unit 200 ends breath measurement processing.

As a result of step S331, in a case where all of the plurality of acquired still images are the images of the same person (S331→Yes), a plurality of images acquired from the video or frame capturing in step S321 are stored as the first image group in the storage device 25 (S333), and the processing returns to step S600 of FIG. 11. The first image group corresponds to the images P10 to P13 in FIG. 2.

(Breath Alcohol Determination Processing)

FIG. 14 is a flowchart showing a detailed procedure of breath alcohol determination processing (S500) in FIG. 11. When breath is introduced at step S204 in FIG. 11, the water vapor sensor output processing unit 202 of the terminal device 2 determines whether or not an output value Vh of the water vapor sensor 122 is equal to or greater than a threshold Vth1 indicating that sufficient breath introduction is being performed (S501). The predetermined time is, for example, an average time+α (for example, 1 second) at which the output value Vh of the water vapor sensor 122 reaches the threshold Vth1 when an adult introduces breath. As a result of step S501, in a case where the output value Vh of the water vapor sensor 122 is less than the threshold Vth1 (S501→No), the water vapor sensor output processing unit 202 determines whether or not the predetermined time has elapsed since the breath introduction was performed (S502). By performing such determination, it is determined whether or not breath sufficient to calculate each gas concentration which will be described later has been introduced. As a result of step S502, in a case where the predetermined time has not elapsed since breath introduction was performed (S502 No), the water vapor sensor output processing unit 202 returns the processing to step S501. As a result of step S502, in a case where the predetermined time has elapsed since the breath introduction was performed (S502→Yes), the display processing unit 203 displays an error message such as "Because the introduction volume is insufficient, please measure again." or the like on the display input device 22 (S503). Thereafter, re-introduction of breath is performed by the processing unit 200 by returning to step S203 of FIG. 11.

As a result of step S501, in a case where the output value Vh of the water vapor sensor 122 is equal to or greater than the threshold Vth1 (S501→Yes), the gas concentration calculation processing unit 204 calculates the concentration of each gas such as hydrogen, alcohol (ethanol), acetaldehyde, and the like in the breath, based on each output value of the hydrogen sensor 121, the alcohol sensor 124, the acetaldehyde sensor 123, and the like (S511). The gas components detected by these three kinds of gas sensors (hydrogen sensor 121, alcohol sensor 124, and acetaldehyde sensor 123) are main components contained in breath after drinking. By calculating the gas concentration of these three kinds of gas components (hydrogen, the ethanol (alcohol), and acetaldehyde) and analyzing the concentration of these three kinds of gas components by using mathematical method, it is possible to improve the accuracy of the ethanol concentration. Then, the drinking determination processing unit 206 determines whether or not the calculated ethanol (alcohol) gas concentration is less than a drinking threshold (S512).

As a result of step S512, in a case where the ethanol gas (alcohol) concentration is less than the drinking threshold (S512→Yes), the drinking determination processing unit 206 determines that the user has not drunk alcohol (S521), and stores the determination result of step S511 in the storage device 25 in association with the first image group stored in the storage device 25 in step S333 of FIG. 12 (S523). At this time, the respective gas concentrations calculated in step S511 may also be stored in the storage device 25 in association with the first image group. Then, the display processing unit 203 displays the determination result of step S512 on the display input device 22 (S524) and the processing returns to step S600 in FIG. 11. In step S524, permission processing such as unlocking the key of the automobile is not performed.

As a result of step S512, in a case where the ethanol (alcohol) gas concentration is not less than the drinking threshold (S512→No), that is, in a case where any one of the calculated gas concentrations is equal to or greater than the drinking threshold, the drinking determination processing unit 206 determines that the user has drunk alcohol (S531). Then, the alcohol concentration in the blood becomes less than the predetermined value, the possible driving time calculation unit 208 calculates the possible driving time which is a time when the driving is possible (S532) based on the calculated alcohol concentration and the like.

Subsequently, the display processing unit 203 displays the determination result of step S512 and the possible driving time calculated in step S532 on the display input device 22 (S533). Further, the drinking determination processing unit 206 associates the determination result of step S512 and each gas concentration calculated in step S521 with the first image group stored in the storage device 25 in step S333 of FIG. 12 to store in the storage device 25 (S534), and ends the breath measurement processing.

(Second Authentication Processing)

FIG. 15 is a flowchart showing a detailed procedure of the second authentication processing (S600) in FIG. 11. The second authentication processing shown in FIG. 15 is started when it is determined that all of the first image group is the image of the same person in the first authentication processing of FIG. 12, and the user has not drunk in the breath alcohol determination processing of FIG. 14. First, the display processing unit 203 displays information on the result of the breath alcohol determination processing (indicating that the user has not drunk alcohol) and the like in FIG. 14 on the display input device 22 and displays the confirmation button B on the display input device 22 (S601).

Then, the second authentication processing unit 209 determines whether or not the displayed confirmation button B (see FIG. 3) has been selected and input (S602). As a result of step S602, in a case where the confirmation button B is not selected and input (S602→No), the second authentication processing unit 209 determines whether or not a predetermined time has elapsed from the processing in step S601 (S603). As a result of step S603, in a case where the predetermined time has not passed since the processing in step S601 (S603→No), the second authentication processing unit 209 returns the processing to step S602.

As a result of step S603, in a case where the predetermined time has elapsed since the processing of step S601 (S603→Yes), the display processing unit 203 causes the display input device 22 to display an error message prompting re-measurement (S611). Then, the second authentication processing unit 209 erases the respective information stored in the storage device 25 (S612). Thereafter, the processing unit 200 returns the processing to step S203 in FIG. 11.

As a result of step S602, in a case where the confirmation button B is selected and input (S602→Yes), the imaging processing unit 205 causes the imaging device 21 to capture a still image (the second image capturing at the time of the analysis of breath components) (S621). That is, with the confirmation button B displayed on the display input device 22 being selected and input as a trigger, capturing of a still image (capturing a face image of the user) is performed. The captured still image is the second image. The second image corresponds to the image P30 in FIG. 4. In this way, by capturing an image in step S621 after ending the breath alcohol determination processing (S500 in FIG. 11), it is possible to capture an image in step S621 only when the user has not drunk alcohol. That is, the second authentication processing can be performed according to the result of the breath alcohol determination processing (S500 in FIG. 11). Next, the second authentication processing unit 209 determines whether or not the second image captured in step S621 can be subjected to face authentication (S622). Whether face authentication is possible or not depends on whether or not the feature points for authentication used in the first authentication processing are captured.

As a result of step S622, in a case where face authentication is impossible (S622→No), the display processing unit 203 causes the display input device 22 to display a message such as "Please capture an image again." and the confirmation button B (S623), and the processing returns to step S602. As a result of step S622, in a case where face authentication is possible (S622→Yes), the second authentication processing unit 209 compares the first image group stored in the storage device 25 in step S333 in FIG. 12 with the second image, and analyzes whether or not the person in the first image group and the person in the second image are the same person (S631).

Then, as a result of the analysis in step S631, the second authentication processing unit 209 determines whether or not the person in the first image group and the person in the second image are the same person (S632). In steps S631 and S632, the second authentication processing unit 209 may compare all of the images of the first image group and the second image, but one of the first image group (for example, the image P10 at the breath introduction in FIG. 2) may be compared with the person of the second image. In a case where it is determined that the person in the first image group and the person in the second image are not the same person as a result of step S632 (S632 No), the display processing unit 203 causes the display input device 22 to display a message prompting re-introduction of breath (display of re-introduction) (S651). Further, the second authentication processing unit 209 stores the determination result of the first image group, the second image, and step S632 as a set of information in the storage device (S652). Then, the processing unit 200 returns the processing to step S203 in FIG. 11.

In a case where the person in the first image group and the person in the second image are the same person (S632→Yes) as a result of step S632, the second authentication processing unit 209 stores the first image group, the second image, and the determination result of step S632, the output value of each of the sensors 121 to 127 as a set of information in the storage device 25 (S641). Then, the display processing unit 203 displays the result of input device 22 that the authentication is OK (S642). Thereafter, the processing unit 200 performs permission processing as necessary (S643). The permission processing is processing such as unlocking the key of the automobile, displaying the driving permission on the display input device 22, or the like. In a case where the processing of unlocking of the automobile's key is performed, communication between the terminal device 2 and the automobile is necessary.

It is desirable that the information stored in each processing is erased after the breath measurement processing is ended or after about 5 minutes. In this way, for example, it is possible to prevent the image captured in the previous day from being used for the first authentication processing or the second authentication processing.

According to the first embodiment, as the first authentication processing, it is determined whether or not an image P10 (see FIG. 2) in breath introduction and all of the images P11 to P13 (see FIG. 2) captured over a predetermined period after breath introduction or at least the images P10 and P13 are the images of the same person. As a result, it is possible to determine whether or not the user has been changed for a predetermined period of time from the time of breath introduction, and it is possible to prevent impersonation.

Then, as the second authentication processing, it is determined whether or not the persons captured in all or one of P10 to P13 (see FIG. 2) and the image P30 (see FIG. 4) captured after the analysis of the breath components are the same. Thus, it is possible to prevent impersonation. In addition, by performing the first authentication processing and the second authentication processing, it is possible to improve the accuracy of impersonation prevention.

In addition, it is possible to use each determination result as evidence at the time of getting in the automobile, or the like. Then, by using the portable breath introduction device 1 and the terminal device 2, it is possible to improve the convenience for the user. In particular, the portable breath introduction device 1 and the terminal device 2 can be used for breath measurement before getting into the automobile. Further, according to the first embodiment, by setting the breath introduction device 1 and the terminal device 2 as separate devices, it is possible to use the terminal device 2 as a smart phone or a tablet terminal which is generally sold.

Second Embodiment

<Breath Analysis Device 4>

FIG. 16 is a diagram showing an external view of a breath analysis device 4 used in a second embodiment. The breath analysis device (authentication system and portable terminal) 4 shown in FIG. 16 is an integration of the breath introduction device 1 and the terminal device 2 of the first embodiment. Therefore, those having the same functions as those shown in FIG. 1 are denoted by the same reference numerals, and the description here will be omitted. Since the hardware configuration of the breath analysis device 4 is an integration of the processing unit 14 and the terminal device 2 of the breath introduction device 1 in FIG. 6, so the description thereof will be omitted here. Further, since the software functional block of the breath analysis device 4 is an integration of the configuration shown in FIG. 8 and the configuration shown in FIG. 9, the description here will be omitted.

<Flowchart>
(Initial Processing)

FIG. 17 is a flowchart showing a procedure of initial processing used in the second embodiment. In FIG. 17, processing different from FIG. 10 will be described. In FIG. 17, the processing different from FIG. 10 is that the processing of step S101 and step S102 of FIG. 10 powers the breath analysis device 4 on (S101a). Power may be supplied to each of the sensors 121 to 127 by powering the breath analysis device 4 on in step S101a. Alternatively, when the application of breath analysis device 4 (that is, each of the units 100 to 102, 200 to 209 shown in FIGS. 8 and 9) is operated, electric power is supplied to each of the sensors 121 to 127, and the processing in and after step S111 is performed. In addition, in FIG. 17, the processing of steps S113 and S122 in FIG. 10 will be omitted. Other processing is similar to the processing in FIG. 10, therefore the description thereof will be omitted. In addition, in the second embodiment, the entire breath measurement processing, the first authentication processing, the breath alcohol determination processing, and the second authentication processing are the same processing as in FIGS. 11 to 15 of the first embodiment, therefore the illustration and description thereof will be omitted.

According to the second embodiment, by installing the breath introduction device 1 and the terminal device 2 of the first embodiment as an integrated device, it is possible to install or connect to the terminal device 2 of the breath introduction device 1. In this way, it is possible to simplify the operation.

Third Embodiment

<System Configuration Diagram>

FIG. 18 is a diagram showing a configuration of a breath analysis system used in a third embodiment. The breath analysis system shown in FIG. 18 is different from FIG. 6 in that an automobile insurance company 60 is provided with a server 6 capable of communicating with the terminal device 2 via a network 5. The other configurations are the same as in FIG. 6, so the same reference numerals as in FIG. 6 are denoted and the description thereof will be omitted. The server 6 analyzes using the breath measurement information (details will be described later) transmitted from the terminal device 2. In FIG. 18, the breath introduction device 1 and the terminal device 2 of the first embodiment are used, but the breath analysis device 4 (see FIG. 16) of the second embodiment may be used.

<Flowchart>

(Entire Processing)

FIG. 19 is a flowchart showing a procedure of entire breath measurement processing used in the third embodiment. In FIG. 19, processing different from FIG. 11 will be described. In addition, in the third embodiment, the initial processing is the same process as in FIG. 10 (or FIG. 17), therefore the illustration and description thereof will be omitted. Further, the first authentication processing, the breath alcohol determination processing, and the second authentication processing in the third embodiment are the same processing as in FIGS. 11 to 15 of the first embodiment, therefore the illustration and description thereof will be omitted.

First, in the mode selection process of step S202 in FIG. 19, the user selects the analysis mode. The analysis mode is a mode in which breath is periodically introduced to the breath introduction device 1, breath measurement information (details will be described later) is transmitted to the server 6, and the server 6 analyzes the breath measurement information. After step S600, the transmission processing unit 102 of the terminal device 2 transmits the breath measurement information to the server 6 (S711). In the processing of step S711, even if it is determined that the person is not the same person in the first authentication processing and the second authentication processing, and the user has drunk alcohol in the breath alcohol determination processing, it is desirable that the breath measurement information is transmitted to the server 6. The timing at which the breath measurement information is transmitted to the server 6 may be every time the second authentication processing is ended or the breath measurement information accumulated at a predetermined timing may be transmitted collectively. In addition, the timing at which the breath measurement information is transmitted to the server 6 may be periodic, or the user may perform the transmission operation of the breath measurement information. The breath measurement information includes each gas concentration (information on each of the sensors 121 to 127) calculated in step S511 of FIG. 14 and identification information of the terminal device 2. In addition, the breath measurement information may include determination results in the first image group, the second image, the first authentication processing, the breath alcohol determination processing, and the second authentication processing. Each gas concentration contains at least hydrogen concentration, acetaldehyde concentration, or alcohol (ethanol) concentration.

Then, the server 6 installed in the automobile insurance company 60 performs analysis processing to analyze the transmitted breath measurement information (S712). The content of the analysis processing in step S712 and the analysis result will be described later. In the third embodiment, the breath alcohol determination processing (S500) may be omitted.

<Analysis>

Figure 20A:
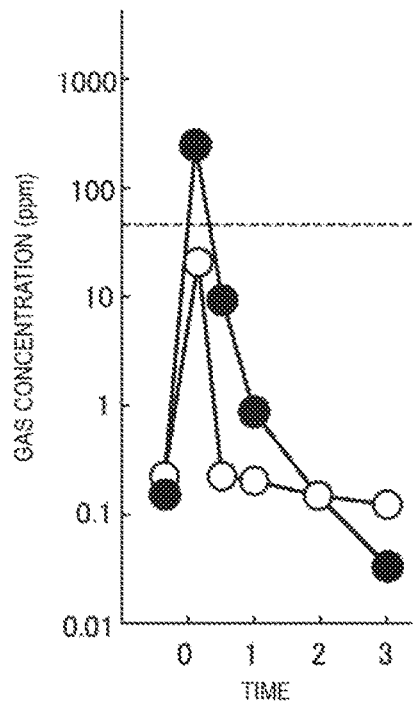
FIG. 20A is a diagram showing the temporal change of gas concentration in introduced breath of ethanol and acetaldehyde of a person resistant to alcohol.
Figure 20B:
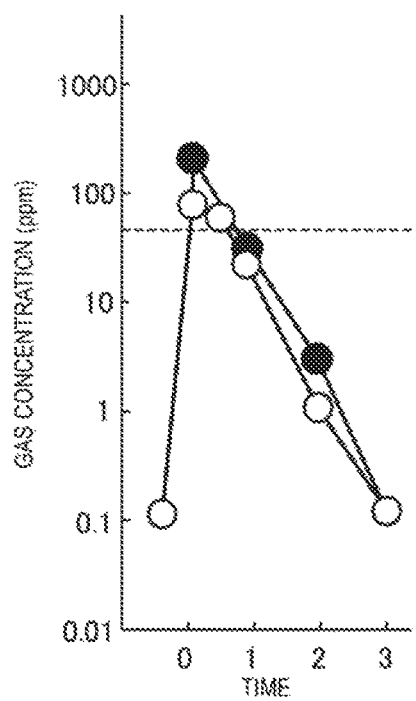
FIG. 20B is a diagram showing the temporal change of gas concentration in introduced breath of ethanol and acetaldehyde of a person vulnerable to alcohol.

FIG. 20 is a diagram showing an example of analysis processing and analysis result performed by the server 6, FIG. 20A is a diagram showing the temporal change of gas concentration in introduced breath of ethanol and acetaldehyde of a person resistant to alcohol, and FIG. 20B is a diagram showing the temporal change of gas concentration in introduced breath of ethanol and acetaldehyde of a person vulnerable to alcohol. In FIGS. 20A and 20B, the vertical axis shows the gas concentration contained in breath and the horizontal axis shows time. In addition, in FIGS. 20A and 20B, filled circles indicate the gas concentration of ethanol and open circles indicate the gas concentration of acetaldehyde. The ethanol is detected by the alcohol sensor 124 shown in FIG. 7.

The analysis in FIG. 20 is in the analysis mode by selecting the analysis mode in the mode selection process in FIG. 19. Therefore, the user introduces breath to the breath introduction device 1 regularly (once every hour in the example of FIG. 20), the breath measurement information thereof is transmitted from the terminal device 2 to the server 6. When FIGS. 20A and 20B are compared, the rate at which the values of the ethanol concentration and the acetaldehyde concentration of a person resistant to alcohol shown in FIG. 20A decrease from the peak values thereof is faster than that of a person vulnerable to alcohol shown in FIG. 20B. That is, the gradient after the peak value of the ethanol concentration and the acetaldehyde concentration of the person resistant to alcohol shown in FIG. 20A is higher than the rate of the person vulnerable to alcohol shown in FIG. 20B.

As an analysis performed on the server 6, the server may calculate the frequency of drinking or estimate the drinking level based on alcohol concentration in breath. Thus, by having the server 6 that receives breath measurement information from the terminal device 2, an organization such as the automobile insurance company 60 or the like can analyze the breath measurement information. In particular, organizations such as the automobile insurance company 60 can analyze users' drinking by including at least hydrogen sensor concentration, acetaldehyde concentration, alcohol (ethanol) concentration (each gas concentration thereof) in the breath measurement information.

FIG. 21 is a diagram showing an example of historical information used in the third embodiment. In FIG. 21, the same components as in FIG. 1 are denoted by the same reference numerals, and the description thereof will be omitted. The breath measurement information transmitted to the server 6 is stored in the server 6, and when there is a request for browsing from the terminal device 2 to the server 6, the server 6 transmits the stored breath measurement information to the terminal device 2. Then, as shown in FIG. 21, the terminal device 2 displays the history of breath measurement information so far on the display input device. In this way, the user can browse the past breath measurement information and use the information for the user's own health management.

According to the third embodiment, it is possible to ensure that the breath measurement information transmitted to the server 6 is the information of the person who introduced breath, thus improving the reliability of the analysis in the server 6.

[Water Vapor Sensor]

(Structure of Water Vapor Sensor 122)

Figure 22A:
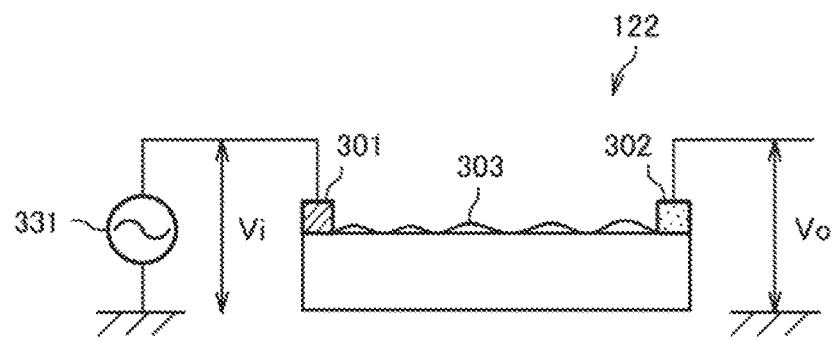
FIG. 22A is a schematic view showing the principle of the water vapor sensor.
Figure 22B:
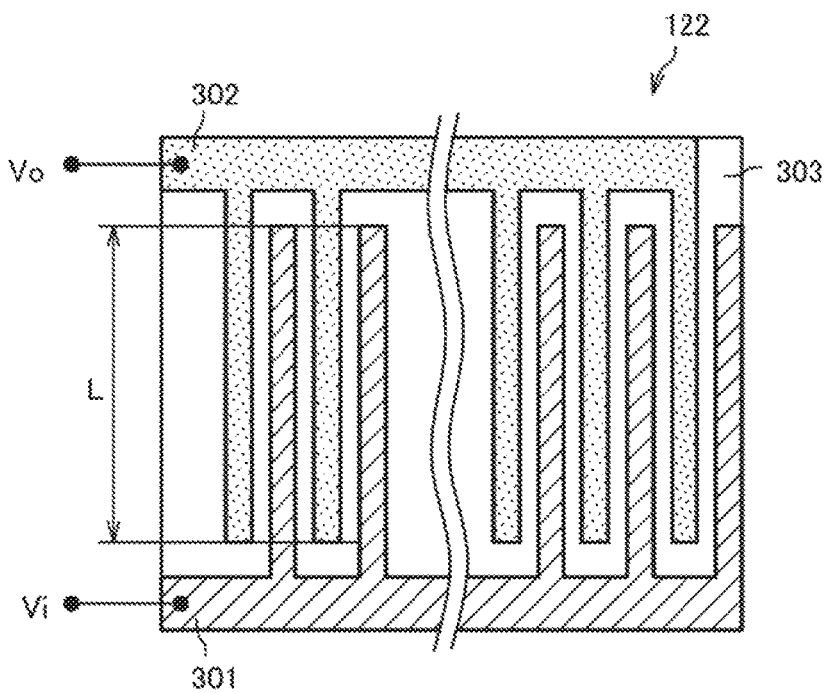
FIG. 22B is a schematic top view of the water vapor sensor.

FIG. 22 is a diagram showing an example of a structure of the water vapor sensor 122 according to the present embodiment, FIG. 22A is a schematic view showing the principle of the water vapor sensor 122, and FIG. 22B is a schematic top view of the water vapor sensor 122. As shown in FIG. 22A, the water vapor sensor 122 is connected to an AC source 331 and includes an application electrode 301 to which an applied voltage Vi is applied by the AC source 331, a detection electrode 302 for detecting a potential Vo at the time of moisture detection, and an insulation portion 303. The AC source 331 corresponds to the power supply 132 and the signal generation device 134 in FIG. 7. In other words, the signal generation device 134 converts a DC voltage generated by the power supply 132 into an AC voltage of a frequency suitable for the water vapor sensor 122. If the power supply 132 is an AC voltage like the AC source 331, the signal generation device 134 does not need to convert to an AC voltage of a frequency suitable for the water vapor sensor 122. Thus, if the power supply 132 is an AC voltage like the AC source 331, the signal generation device 134 can be omitted. The insulation portion 303 is formed of a hydrophilic insulating substrate, specifically, at least the surface is formed of an oxide such as an insulating metal oxide. The shape of the insulation portion 303 may not be in the form of a substrate.

As shown in FIG. 22A, the insulation portion 303 is interposed between the detection electrode 302 and the application electrode 301. Here, the insulation portion 303 has a structure with projections and depressions. The structure of the projections and depressions in the insulation portion 303 will be described later.

<Principle of Saturated Water Vapor Detection>

Figure 23A:
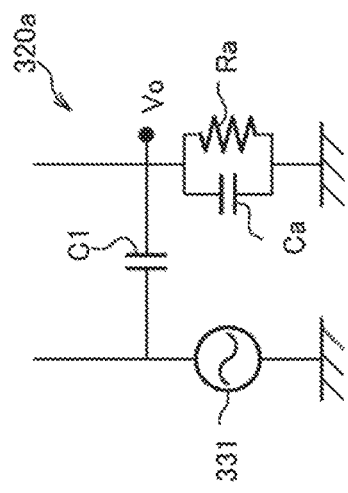
FIG. 23A is a schematic view showing the principle of the water vapor sensor before moisture adhesion.
Figure 23B:
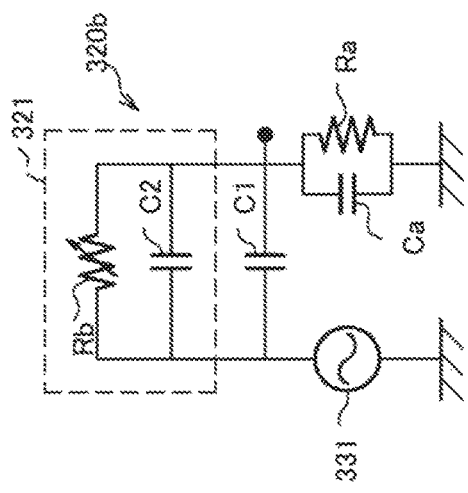
FIG. 23B is an equivalent circuit of the water vapor sensor before moisture adhesion.
Figure 23C:
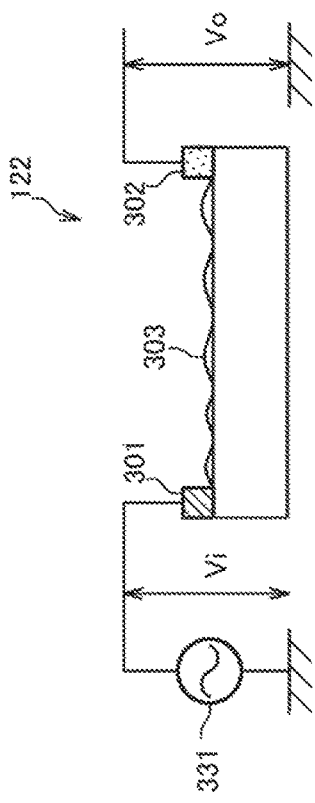
FIG. 23C is a schematic diagram showing the principle of the water vapor sensor after moisture adhesion.
Figure 23D:
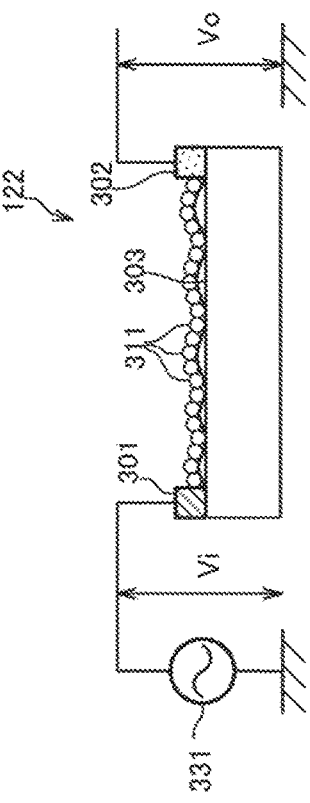
FIG. 23D is an equivalent circuit of the water vapor sensor after moisture adhesion.

FIG. 23 is a diagram describing the principle (state) by which the water vapor sensor 122 that detects saturated water vapor according to the present embodiment, FIG. 23A is a schematic view showing the principle (state) of the water vapor sensor 122 before moisture adhesion, FIG. 23B is an equivalent circuit of the water vapor sensor 122 before moisture adhesion, FIG. 23C is a schematic diagram showing the principle of the water vapor sensor 122 after moisture adhesion, and FIG. 23D is an equivalent circuit of the water vapor sensor 122 after moisture adhesion. The configurations shown in FIG. 23A and FIG. 23C are the same as those shown in FIG. 22A, so the same reference numerals are given and the description thereof will be omitted.

As shown in FIG. 23A, before the moisture adhesion, since the detection electrode 302 and the application electrode 301 are connected to the insulation portion 303, the detection electrode 302 and the application electrode 301 are not energized therebetween. Therefore, an AC voltage is applied to the application electrode 301, but no voltage is detected from the detection electrode 302.

When moisture adheres to the insulation portion 303 of the water vapor sensor 122, a water molecule 311 adheres to the insulation portion 303 as shown in FIG. 23C. As a result, the detection electrode 302 and the application electrode 301 are energized using the water molecule 311 as a path. Then, the voltage applied to the application electrode 301 from the detection electrode 302 is detected (output). Based on the voltage detected (output) in this manner, the water vapor sensor 122 detects moisture (saturated water vapor).

Next, the changes in the equivalent circuit of the water vapor sensor 122 before and after moisture adhesion are compared. Before moisture adhesion, the circuit remains as an equivalent circuit 320a as shown in FIG. 23B. Here, a capacitor C1 is a capacitor indicating the insulation portion 303. Since the distance between the detection electrode 302 and the application electrode 301 is sufficiently large, the capacitance of the capacitor C1 is a small value (<<1). Therefore, the capacitance reactance of the equivalent circuit 320a shown in FIG. 23B is a large value, and the detection electrode 302 and the application electrode 301 are in a state of being almost not energized therebetween. By the way, a circuit composed of a capacitor Ca and a resistor Ra is the equivalent circuit of the atmosphere or the like.

Here, after the moisture adhesion with moisture included in breath attached, the equivalent circuit 320a shown in FIG. 23B becomes the equivalent circuit 320b shown in FIG. 23D. In the equivalent circuit 320b, the circuit 321 indicated by a resistor Rb and a capacitor C2 is an equivalent circuit of the water molecule 311. As shown in FIG. 23C, when moisture (water molecule 311) adheres to the insulation portion 303, the resistor Rb and the capacitor C2 derived from the water molecule 311 are generated as shown in FIG. 23D, and the impedance changes (decreases) by the resistor Rb and the capacitor C2. As a result, the detection electrode 302 and the application electrode 301 are energized therebetween, and a voltage can be detected from the detection electrode 302. Therefore, it is possible to improve responsiveness by detecting the moisture in breath by using the impedance change of the water vapor sensor 122 due to moisture (water molecule 311) adhering to the insulation portion 303. As shown in FIG. 23B, in order for moisture (the water molecule 311) to adhere to the insulation portion 303 so that the detection electrode 302 and the application electrode 301 are energized therebetween, the air applied to the water vapor sensor 122 needs to be saturated water vapor. Therefore, saturated water vapor can be detected with the water vapor sensor 122 shown in FIGS. 22 and 23.

As shown in FIG. 22B, the detection electrode 302 and the application electrode 301 have a comb teeth shape. The detection electrode 302 and the application electrode 301 are disposed on the insulation portion 303 so that the comb teeth of the detection electrode 302 and the application electrode 301 face each other by meshing engagement. In this way, the area of the moisture adhesion part (reaction part) can be increased.

In this way, the water vapor sensor 122 shown in FIGS. 22 and 23 is designed to detect breath of high humidity (saturated water vapor state). In other words, the water vapor sensor 122 is designed to detect whether or not outside air (breath) introduced from the breath introduction inlet 11 (see FIG. 1) is saturated water vapor. Therefore, it is not necessary to measure the moisture amount in the air and it is sufficient to detect high humidity air (breath). Incidentally, the human body temperature is about 36° C., the high humidity breath introduced from the human body is cooled by contact with the outside air or the breath introduction device 1 (see FIG. 1) and maintains the saturation state.

As shown in FIG. 22, the water vapor sensor 122 according to the present embodiment has a configuration in which the insulation portion 303 is interposed between the detection electrode 302 and the application electrode 301. Then, as shown in FIG. 23C, the water molecule 311 included in breath adheres to the insulation portion 303, therefore energization is performed with the water molecule 311 as a pass. As a result, the output voltage is detected at the detection electrode 302. Therefore, in the water vapor sensor 122 according to the present embodiment, it is sufficient to provide the insulation portion 303 with such a size that the water molecule 311 can be adhered, and miniaturization can be realized.

In addition, before the moisture (water molecule 311) adheres to the insulation portion 303, the output voltage can be almost 0, whereas after the moisture (water molecule 311) adheres, the output voltage can be approximately Vi (the applied voltage). As a result, an excellent Signal/Noise (S/N) ratio can be realized.

In the water vapor sensor 122, as described above, the surface of the insulation portion 303 has a structure with projections and depressions. In this way, since the surface of the insulation portion 303 has projections and depressions, the surface area of the insulation portion 303 can be increased. That is, since the surface of the insulation portion 303 has projections and depressions, more water molecules 311 can adhere, the output voltage can be increased, and therefore higher sensitivity can be achieved. Further, by making at least the surface of the insulation portion 303 be formed of an oxide (metal oxide) with high hydrophilicity, moisture can easily adhere.

In addition, the water vapor sensor 122 may not have the configuration shown in FIGS. 22 and 23. In addition, instead of the water vapor sensor 122, the humidity sensor 127 may be used.

In the first embodiment, the breath introduction device 1 and the terminal device 2 are connected by the cable 3, but the breath introduction device 1 and the terminal device 2 may transmit and receive information by wireless communication. In addition, the breath introduction device 1 may be provided with a voice input device such as a microphone, voice may be input together with breath introduction by introducing breath while the user speaks out. The terminal device 2 may store voice information of the user in the storage device 25 beforehand, and it may be determined whether or not the voice input together with breath introduction is the one of the user by comparing the voice input together with the breath introduction with the previously stored voice information. In this way, it is possible to improve the reliability of authentication. In addition, a message such as "Please blow your breath with the countdown number displayed." or the like may be displayed on the display input device 22 of the terminal device 2, and breath introduction and capturing of the first image group may be performed with the countdown as a trigger.

In addition, in the present embodiment, video or frame capturing is performed for a predetermined time in the first authentication, but the present embodiment is not limited thereto. For example, in step S311 of FIG. 12, when video or frame capturing is started and the confirmation button B is selected and input (step S621 in FIG. 15), the video and the frame capturing may be ended. In this case, the images from the start of the breath introduction until just before the confirmation button B is selected and input become the first image group, and the image immediately after the confirmation button B is selected and input becomes the second image. In this case, steps S321 to S333 in FIG. 12 and steps S622 to S652 in FIG. 15 are performed in parallel.

In addition, the imaging device 21 may be provided in the breath introduction device 1. In this case, the user can use (introduce breath) in a state with the terminal device 2 and the breath introduction device 1 separated.

The present invention is not limited to the embodiments described above, but includes various modifications. For example, the above-described embodiments have been described in detail in order to explain the present invention in an easy-to-understand manner, and are not necessarily limited to those having all the configurations described. In addition, it is possible to replace a part of a configuration of one embodiment with a configuration of another embodiment, and the configuration of another embodiment can be added to the configuration of one embodiment. In addition, it is possible to add, delete and replace other configurations with respect to part of the configuration of each embodiment.

In addition, each of the above-described configurations, functions, units 100 to 102, 200 to 209, storage devices 16 and 25, and the like may be realized by hardware, for example, by designing some or all thereof in an integrated circuit. In addition, as shown in FIGS. 6 to 9, each configuration, function, and the like described above can be realized by software by interpreting and executing programs which realize the respective functions by the processor such as the CPUs 23, 141, and the like. Information such the programs, tables, files, and the like that realize each function can be stored in recording devices such as memories 24 and 142, a Solid State Drive (SSD), an Integrated Circuit (IC) card, a Secure Digital (SD) card, a Digital Versatile Disc (DVD), or the like in addition to Hard Disk (HD). In addition, in each of the embodiments, a control line or a information line indicates what is considered to be necessary for the description, and all the control lines or information lines are not necessarily shown on a product. In reality, it may be considered that almost all components are interconnected to each other.

REFERENCE SIGNS LIST 1 breath introduction device (authentication system)
2 terminal device (authentication system, portable terminal)
3 cable
4 breath analysis device (authentication system, mobile terminal)
6 server (second analysis unit, the authentication system)
11 breath introduction inlet (breath introduction unit)
12 sensor device (breath detection unit)
21 imaging device (imaging unit)
22 display input device (display unit)
100, 200 processing unit
101 determination unit
121 hydrogen sensor (detection element)
122 water vapor sensor (saturated water vapor detection element)
123 acetaldehyde sensor (detection element)
124 alcohol sensor (detection element)
201 output value processing unit 202 water vapor sensor output processing unit (breath analysis unit)
203 display processing unit
204 gas concentration calculation processing unit (breath analysis unit)
205 imaging processing unit (imaging control unit)
206 drinking determination processing unit
207 first authentication processing unit (image analysis unit)
208 possible driving time calculation unit
209 second authentication processing unit (image analysis unit)
B confirmation button (symbol)

The invention claimed is:

1. An authentication system for detecting breath alcohol, comprising:
a breath introduction unit into which a breath of a person is introduced;
an imaging unit that captures images of a face of the person blowing the breath into the breath introduction unit;
a sensor device that detects breath components including an alcohol component contained in the introduced breath from the breath introduction unit; and
at least one processor programmed to:
control the imaging unit;
analyze the breath components including the alcohol component of the breath components detected by the sensor device; and
analyze the images captured by the imaging unit,
control the imaging unit to perform first image capturing during the introduction of the breath into the breath introduction unit and second image capturing after the analyzing of the breath components,
output a result as to whether or not the images captured during the first image capturing and the second image capturing are both of the same person,
wherein the breath introduction unit and the sensor device are configured to be mounted on a portable terminal accommodated in a portable housing and provided with the imaging unit or accommodated in the same housing as the portable terminal provided with the imaging unit,
wherein the sensor device includes a saturated water vapor detection element for detecting whether or not the introduced breath from the breath introduction unit is saturated water vapor and has a sufficient introduction volume, and
the saturated water vapor detection element includes:
an insulation portion formed of insulating material;
an application unit to which a voltage is applied; and
wherein the saturated water vapor detection element outputs a voltage signal according to a current flowing into an electric path through a water molecule adhered to a surface of the insulating material by the voltage applied to the application unit.

2. The authentication system for detecting breath alcohol according to claim 1, wherein the at least one processor is further programmed to:
to capture images of the person in a video or a plurality of time-series still images as the first image capturing, and determine whether or not each image at a plurality of points in time acquired from the video is of the same person, or whether or not each image in the plurality of still images is of the same person.

3. The authentication system for detecting breath alcohol according to claim 1, wherein the at least one processor is further programmed to:
start the first image capturing when the sensor device detects the components of the breath.

4. An authentication system for detecting breath alcohol, comprising:
a breath introduction unit into which a breath of a person is introduced;
an imaging unit that captures images of a face of the person blowing the breath on the breath introduction unit;
a sensor device that detects breath components including an alcohol component contained in the introduced breath from the breath introduction unit; and
at least one processor programmed to:
control the imaging unit;
analyze the breath components including the alcohol component of the breath components detected by the sensor device; and
analyzing the images captured by the imaging unit,
control the imaging unit to perform first image capturing during the introduction of the breath into the breath introduction unit and second image capturing after the analyzing of the breath components,
output a result as to whether or not the images captured during the first image capturing and the second image capturing are both of the same person,
wherein the breath introduction unit and the sensor device are configured to be mounted on a portable terminal accommodated in a portable housing and provided with the imaging unit or accommodated in the same housing as the portable terminal provided with the imaging unit,
start the first image capturing when the sensor device detects the components of the breath,
wherein the sensor device includes a saturated water vapor detection element for detecting whether or not the introduced breath is saturated water vapor and has a sufficient introduction volume, and
the first image capturing is started when an output value of the saturated water vapor detection element exceeds a predetermined threshold.

5. The authentication system for detecting breath alcohol according to claim 1,
wherein the breath introduction unit and the imaging unit are arranged so that at least a mouth of the person is captured in the images obtained by the first image capturing.

6. An authentication system for detecting breath alcohol, comprising:
a breath introduction unit into which a breath of a person is introduced;
an imaging unit that captures images of a face of the person blowing the breath on the breath introduction unit;
a sensor device that detects breath components including an alcohol component contained in the introduced breath from the breath introduction unit; and
at least one processor programmed to:
control the imaging unit;
analyzing the breath components including the alcohol component of the breath components detected by the sensor device; and
analyze the images captured by the imaging unit,
control the imaging unit to perform first image capturing during the introduction of the breath into the breath introduction unit and second image capturing after the analyzing of the breath components, output a result as to whether or not the images captured during the first image capturing and the second image capturing are both of the same person,
wherein the breath introduction unit and the sensor device are configured to be mounted on a portable terminal accommodated in a portable housing and provided with the imaging unit or accommodated in the same housing as the portable terminal provided with the imaging unit, and
wherein the second image capturing is performed when a symbol displayed in a display unit, with a result of the analyzing of the breath components, is selected and input.

7. The authentication system for detecting breath alcohol according to claim 6,
wherein the analysis of the breath includes determination of drinking alcohol based on the alcohol component.

8. The authentication system for detecting breath alcohol according to claim 1,
wherein the distance between the breath introduction unit and the imaging unit is 5 cm or less.

9. The authentication system for detecting breath alcohol according to claim 1,
wherein in a case where the breath introduction unit and the sensor device are configured to be mounted on the portable terminal accommodated in the portable housing and provided with the imaging unit,
when the breath introduction unit and the sensor device are connected to the portable terminal by a cable, the breath introduction unit and the sensor device are powered on.

10. The authentication system for detecting breath alcohol according to claim 1, further comprising:
at least one other processor that is provided in a device different from a device provided with the sensor device and is capable of communicating with the device provided with the sensor device,
wherein information on the breath components detected by the sensor device is transmitted to the at least one other processor at a predetermined timing, and
the at least one other processor is programmed to analyze the transmitted information on the breath components.

11. The authentication system for detecting breath alcohol according to claim 10,
wherein the sensor device is provided with detection elements for detecting at least hydrogen, acetaldehyde, and ethanol, and
the information on the breath components contains at least information on an output value of each detection element.

12. The authentication system for detecting breath alcohol according to claim 10, further comprising:
a display unit where a user can view the information on the breath components transmitted to the at least one other processor.

13. An authentication method for detecting breath alcohol in an authentication system including:
a breath introduction unit into which a breath of a person is introduced,
an imaging unit that captures images of a face of the person blowing the breath into the breath introduction unit,
a sensor device that detects components including an alcohol component contained in the introduced breath from the breath introduction unit, and
at least one processor programmed to:
control the imaging unit,
analyze the breath components including the alcohol component of the breath components detected by the sensor device, and
analyze the images captured by the imaging unit,
the breath introduction unit and the sensor device being configured to be mounted on a portable terminal accommodated in a portable housing and provided with the imaging unit or accommodated in the same housing as the portable terminal provided with the imaging unit,
the method comprising:
controlling the imaging unit to perform first image capturing during introduction of the breath into the breath introduction unit and second image capturing after the analyzing of the breath components; and
outputting a result as to whether or not the images captured during the first image capturing and the second image capturing are both of the same person; and
controlling the imaging unit to perform the second image capturing when a symbol displayed in a display unit, with a result of the analyzing of the breath components, is selected and input.

* * * * *